United States Patent
Wong

(10) Patent No.: US 7,077,838 B2
(45) Date of Patent: Jul. 18, 2006

(54) VARIABLE REPETITION RATE FIRING SCHEME FOR REFRACTIVE LASER SYSTEMS

(75) Inventor: Jonathan Wong, Santa Clara, CA (US)

(73) Assignee: VISX, Incorporated, Santa Clara, CA (US)

( * ) Notice: Subject to any disclaimer, the term of this patent is extended or adjusted under 35 U.S.C. 154(b) by 239 days.

(21) Appl. No.: 10/447,665

(22) Filed: May 28, 2003

(65) Prior Publication Data

US 2005/0102008 A1    May 12, 2005

Related U.S. Application Data

(60) Provisional application No. 60/384,621, filed on May 30, 2002.

(51) Int. Cl.
*A61B 18/18* (2006.01)

(52) U.S. Cl. .................. 606/5; 606/4; 606/10

(58) Field of Classification Search ............ 606/4, 606/5, 10; 607/88; 128/898
See application file for complete search history.

(56) References Cited

U.S. PATENT DOCUMENTS

| | | | |
|---|---|---|---|
| 4,665,913 A | 5/1987 | L'Esperance, Jr. | |
| 4,941,093 A | 7/1990 | Marshall et al. | |
| 5,061,342 A | 10/1991 | Jones | |
| 5,137,530 A | 8/1992 | Sand | |
| 5,144,630 A | 9/1992 | Lin | |
| 5,163,934 A * | 11/1992 | Munnerlyn | 606/5 |
| 5,170,191 A | 12/1992 | Jones | |
| 5,240,553 A | 8/1993 | Jones | |
| 5,294,293 A | 3/1994 | Jones | |
| 5,348,551 A | 9/1994 | Spears et al. | |
| 5,520,679 A * | 5/1996 | Lin | 606/5 |
| 5,646,791 A | 7/1997 | Glockler | |
| 5,683,379 A | 11/1997 | Hohla | |
| 5,713,892 A | 2/1998 | Shimmick | |
| 5,742,626 A | 4/1998 | Mead et al. | |
| 5,800,424 A | 9/1998 | Sumiya | |

(Continued)

OTHER PUBLICATIONS

Borsuztky et al., "Tunable UV Radiation at Short Wavelengths (188-240 nm) Generated by Sum Frequency Mixing in Lithium Borate", *Appl. Phys.* 61:529-532 (1995).

*Primary Examiner*—A. Farah
(74) *Attorney, Agent, or Firm*—Townsend&Townsend&Crew LLP; Mark D. Barrish

(57) ABSTRACT

Systems and methods apply pulsed laser energy to an eye with a pulsed laser system. The laser system includes a pulsed laser, a laser beam delivery system and at least one processor. The laser makes a beam of an ablative light energy. A dimension across the laser beam varies during a treatment of the eye. A firing rate of the laser varies as the dimension across the beam varies during the treatment. The dimension across the beam and the firing rate of the laser can be arranged so as to maintain a power of the beam applied to the eye at a substantially constant level during at least a portion of the treatment. A firing rate of the laser for each pulse may be listed in a treatment table.

26 Claims, 8 Drawing Sheets

U.S. PATENT DOCUMENTS

| | | |
|---|---|---|
| 5,807,379 A | 9/1998 | L'Esperance, Jr. |
| 5,827,264 A * | 10/1998 | Hohla .......................... 606/5 |
| 5,912,775 A | 6/1999 | Glockler |
| 5,993,441 A | 11/1999 | Muller et al. |
| 6,080,148 A | 6/2000 | Damasco et al. |
| 6,190,377 B1 | 2/2001 | Kuzdrall |
| 6,203,539 B1 * | 3/2001 | Shimmick et al. ............. 606/5 |
| 6,245,059 B1 | 6/2001 | Clapham |
| 6,271,914 B1 | 8/2001 | Frey et al. |
| 6,331,177 B1 | 12/2001 | Munnerlyn et al. |
| 6,482,199 B1 | 11/2002 | Neev |
| 2002/0035359 A1 | 3/2002 | Yee et al. |

* cited by examiner

```
                150  152
                  \   \                                    ← 140
Patient Name ——————\   \ 154
reprate ———————— variable /
Patient ID ———————————— 156
Eye ——————— OD  ———— 158   160
Refraction ——————— -3    -2.25 /   60         0
Pulse Count          1079
Pulse No.  Iris Diam  Slit Width  Slit Axis  X (mm)  Y (mm)  Delay (ms)
    1         1.5        6.5          0       -0.4    0.2       50
    2         1.5        6.5          0        0.3   -0.6       50
    3         1.5        6.5          0       -0.1     0        50
    4         1.5        6.5          0        0.2     1        50
    5         1.5        6.5          0       -0.3   -0.8       50
    6         1.5        6.5          0        1.7    0.1       50
    7         1.5        6.5          0        0.6   -1.5       50
    )         (          \          )        (       )         (
   170       172        174        176       178     180       182
```

FIG. 6

| Diameter | Area (cm2) | Delay (ms) | Firing Rate (Hz) | Fluence (mj/cm2) | Energy (mJ) | Power (mW) |
|---|---|---|---|---|---|---|
| 6.5 | 0.332 | 125 | 8.00 | 160 | 53.07 | 424.5 |
| 6 | 0.283 | 111 | 9.01 | 160 | 45.22 | 407.4 |
| 5.5 | 0.237 | 91 | 10.99 | 160 | 37.99 | 417.5 |
| 5 | 0.196 | 77 | 12.99 | 160 | 31.40 | 407.8 |
| 4.5 | 0.159 | 63 | 12.99 | 160 | 25.43 | 403.7 |
| 4 | 0.126 | 50 | 15.87 | 160 | 20.10 | 401.9 |
| 3.5 | 0.096 | 50 | 20.00 | 160 | 15.39 | 307.7 |
| 3 | 0.071 | 50 | 20.00 | 160 | 11.30 | 226.1 |
| 2.5 | 0.049 | 50 | 20.00 | 160 | 7.85 | 157.0 |
| 2 | 0.031 | 50 | 20.00 | 160 | 5.02 | 100.5 |
| 1.5 | 0.018 | 50 | 20.00 | 160 | 2.83 | 56.5 |
| 1 | 0.008 | 50 | 20.00 | 160 | 1.26 | 25.1 |
| 0.5 | 0.002 | 50 | 20.00 | 160 | 0.31 | 6.3 |
| 202 | 204 | 206 | 208 | 210 | 212 | 214 |

FIG. 7

| Diameter | Area (cm2) | Power | Fluence | Energy (mJ) | Firing Rate |
|---|---|---|---|---|---|
| 6.5 | 0.332 | 400 | 160 | 53.07 | 8 |
| 6 | 0.283 | 400 | 160 | 45.22 | 9 |
| 5.5 | 0.237 | 400 | 160 | 37.99 | 10 |
| 5 | 0.196 | 400 | 160 | 31.40 | 13 |
| 4.5 | 0.159 | 400 | 160 | 25.43 | 16 |
| 4 | 0.126 | 400 | 160 | 20.10 | 20 |
| 3.5 | 0.096 | 400 | 160 | 15.39 | 26 |
| 3 | 0.071 | 400 | 160 | 11.30 | 35 |
| 2.5 | 0.049 | 400 | 160 | 7.85 | 51 |
| 2 | 0.031 | 400 | 160 | 5.02 | 80 |
| 1.5 | 0.018 | 400 | 160 | 2.83 | 142 |
| 1 | 0.008 | 400 | 160 | 1.26 | 318 |
| 0.5 | 0.002 | 400 | 160 | 0.31 | 1274 |
| 202 | 204 | 214 | 210 | 212 | 208 |

FIG. 8

VARIABLE REPETITION RATE FIRING SCHEME FOR REFRACTIVE LASER SYSTEMS

CROSS-REFERENCE TO RELATED APPLICATION

This is a non-provisional patent application which claims priority from U.S. Provisional Patent Application No. 60/384,621 filed May. 30, 2002, the full disclosure of which is incorporated herein by reference.

BACKGROUND OF THE INVENTION

The present invention is generally related to correcting optical errors of light refracted by eyes. In exemplary embodiments, the invention provides devices, systems, and methods for correction of optical errors of eyes, and is particularly well-suited for the treatment of eyes during in situ keratomiliusis (LASIK), photorefractive keratectomy (PRK) and the like.

Known laser eye surgery procedures generally employ an ultraviolet or infrared laser to remove a microscopic layer of stromal tissue from the cornea of the eye. The laser typically removes a selected shape of the corneal tissue, often to correct refractive errors of the eye. Ultraviolet laser ablation results in photodecomposition of the corneal tissue, but generally does not cause significant thermal damage to adjacent and underlying tissues of the eye. The irradiated molecules are broken into smaller volatile fragments photochemically, directly breaking the intermolecular bonds.

Laser ablation procedures can remove the targeted stroma of the cornea to change the cornea's contour for varying purposes, such as for correcting myopia, hyperopia, astigmatism, and the like. Control over the distribution of ablation energy across the cornea may be provided by a variety of systems and methods, including the use of ablatable masks, fixed and moveable apertures, controlled scanning systems, eye movement tracking mechanisms, and the like. In known systems, the laser beam often comprises a series of discrete pulses of laser light energy, with the total shape and amount of tissue removed being determined by the shape, size, location, and/or number of laser energy pulses impinging on the cornea. A variety of algorithms may be used to calculate the pattern of laser pulses used to reshape the cornea so as to correct a refractive error of the eye. Known systems make use of a variety of forms of lasers and/or laser energy to effect the correction, including infrared lasers, ultraviolet lasers, femtosecond lasers, wavelength multiplied solid-state lasers, and the like. The lasers of these laser systems typically deliver a series of laser beam pulses during a treatment.

Work in connection with the present invention suggests that the known methodology for a laser ablation treatment may be less than ideal. It is generally desirable to complete a surgical procedure as quickly as possible. However, if the treatment occurs too quickly, tissue can heat excessively, potentially resulting in undesirable complications. Extended treatment times are uncomfortable for patients and time consuming for surgical staff. Also, it has been suggested by some surgeons that extended treatment times can vary tissue hydration that may change an amount of correction received by a patient.

In light of the above, it would be desirable to provide surgical ablation treatments having reduced treatment times while avoiding at least some of the limitations of known systems.

BRIEF SUMMARY OF THE INVENTION

The present invention provides systems and methods for applying pulsed energy to an eye in which the energy applied to the eye with a pulse of the beam varies during a treatment. A firing rate of the pulsed energy may vary in correlation with the energy applied to the eye with a pulse of the laser beam during the treatment.

In a first aspect, the invention provides a method of treating an eye with a laser. The laser makes a beam of an ablative light energy. A dimension across the laser beam varies during a treatment of the eye. A firing rate of the laser varies during the treatment in correlation with the varying dimension across the beam. In some embodiments, the dimension across the beam and the firing rate may vary and be arranged so as to maintain a power of the beam applied to the eye at a substantially constant level during at least a portion of the treatment.

In some embodiments, the dimension across the beam may vary between a first size and a second size, and an amount of energy applied to the eye with a first pulse of the laser beam may be lower at the first size than an amount of energy applied to the eye with a second pulse of the laser beam at the second size. The firing rate may vary between a first firing rate at the first size and a second rate at the second size with the first firing rate being faster than the second firing rate.

In another embodiment, the dimension across the beam may vary between a first size and a second size, and an amount of energy applied to the eye with a first pulse of the laser beam may be higher at the first size than an amount of energy applied to the eye with a second pulse of the laser beam at the second size. The firing rate may vary between a first firing rate at the first size and a second rate at the second size with the first firing rate being slower than the second firing rate.

In specific embodiments, the laser beam may scan over a treatment area of the eye. The dimension across the beam may vary by at least 0.5 mm during the ablative treatment. Further, the dimension across the beam may vary by at least 3 mm during the ablative treatment. The firing rate of the laser may vary by at least 2 Hz during the treatment. Further, the firing rate of the laser may vary by at least 10 Hz during the treatment. The laser may be a pulsed laser, and the laser beam may be a pulsed laser beam having a pulse duration. Also, the firing of the pulsed laser may be delayed in response to predetermined value.

In an embodiment, a series of corneal ablation laser pulses may be directed toward the eye with a first pulse having a first size and a second pulse having a second size which is smaller than the first size, and a firing rate of the series may vary in response to the sizes to effect a faster firing rate for the second pulse than during the first pulse.

In another embodiment, a series of corneal ablation laser pulses may be directed toward the eye with a first pulse having a first size and a second pulse having a second size which is larger than the first size; and a firing rate of the series may vary in response to the sizes to effect a slower firing rate for the second pulse than for the first pulse.

In another aspect the invention provides a system for treating an eye with a laser beam. The system includes a laser for making a beam of an ablative light energy. At least one processor having a computer program is adapted to vary a dimension across the laser beam during a treatment of the eye and vary a firing rate of the laser beam during the treatment in correlation with the varying dimension across the beam. In some embodiments, the dimension across the beam and the firing rate of the laser are arranged so as to maintain a power of the beam applied to the eye at a substantially constant level during at least a portion of the treatment.

In some embodiments, the dimension across the beam varies between a first size and a second size, and an amount of energy applied to the eye with a first pulse of the laser beam is lower at the first size than an amount of energy applied to the eye with a second pulse of the laser beam at the second size. The firing rate varies between a first firing rate at the first size and a second rate at the second size, and the first rate is faster than the second rate.

In additional embodiments, the dimension across the beam varies between a first size and a second size, and an amount of energy applied to the eye with a first pulse of the laser beam is higher at the first size than an amount of energy applied to the eye with a second pulse of the laser beam at the second size. The firing rate varies between a first firing rate at the first size and a second rate at the second size, and the first rate is slower than the second firing rate.

In specific embodiments, the computer program of the at least one processor is further adapted to scan the laser beam over a treatment area. The dimension across the beam varies by at least 0.5 mm during the ablative treatment, and the dimension across the beam may vary by at least 3 mm during the ablative treatment. The laser firing rate varies by at least 2 Hz during the treatment, and the firing rate of the laser may vary by at least 10 Hz during the treatment. The laser is a pulsed laser, and the laser beam is a pulsed laser beam having a pulse duration. The processor further includes a treatment table listing a predetermined delay between sequential pulses of the pulsed laser beam.

In an embodiment a laser eye surgery system for treating an eye includes a laser generating a series of laser pulses, and delivery optics varying a size of the pulses from a first pulse size to a second pulse size smaller than the first size. A controller varies a firing rate of the laser at least in part in response to the pulse size so that the firing rate is faster during the second pulse size.

In another embodiment a laser eye surgery system for treating an eye includes a laser generating a series of laser pulses, and delivery optics varying a size of the pulses from a first pulse size to a second pulse size larger than the first size. A controller varies a firing rate of the laser at least in part in response to the pulse size so that the firing rate is slower during the second pulse size.

BRIEF DESCRIPTION OF THE DRAWINGS

FIG. 6 illustrates a laser treatment table in accord with an embodiment the invention.

FIG. 7 illustrates treatment diameters and laser firing rates in accord with an embodiment of the invention using a variable laser firing rate for a first portion of a treatment and a fixed firing rate for a second portion of a treatment.

FIG. 8 illustrates variable treatment diameters and laser firing rates arranged so as to maintain a power of the beam applied to the eye at a substantially constant level in accord with an embodiment of the invention.

DETAILED DESCRIPTION OF THE INVENTION

The present invention is particularly useful for enhancing the accuracy and efficacy of laser eye surgical procedures, such as photorefractive keratectomy (PRK), phototherapeutic keratectomy (PTK), laser in situ keratomileusis (LASIK), and the like. Preferably, the present invention can provide enhanced optical accuracy of refractive procedures by improving the treatment time of a refractive treatment program. Hence, while the system and methods of the present invention are described primarily in the context of a laser eye surgery system for treating a cornea of the eye, it should be understood the techniques of the present invention may be adapted for use in alternative eye treatment procedures and systems such as the manufacture of spectacles contact lenses, and the like.

The techniques of the present invention can be readily adapted for use with existing laser systems. By providing a more rapid (and hence, may be less prone to error) methodology for correcting optical errors of an eye, the present invention facilitates sculpting of the cornea so that treated eyes may regularly receive a desired optical correction having improved vision with minimal discomfort to a patient.

As used herein a substantially constant power level encompasses a power level that is stable to within about 25% of an average power level.

Figure 1:
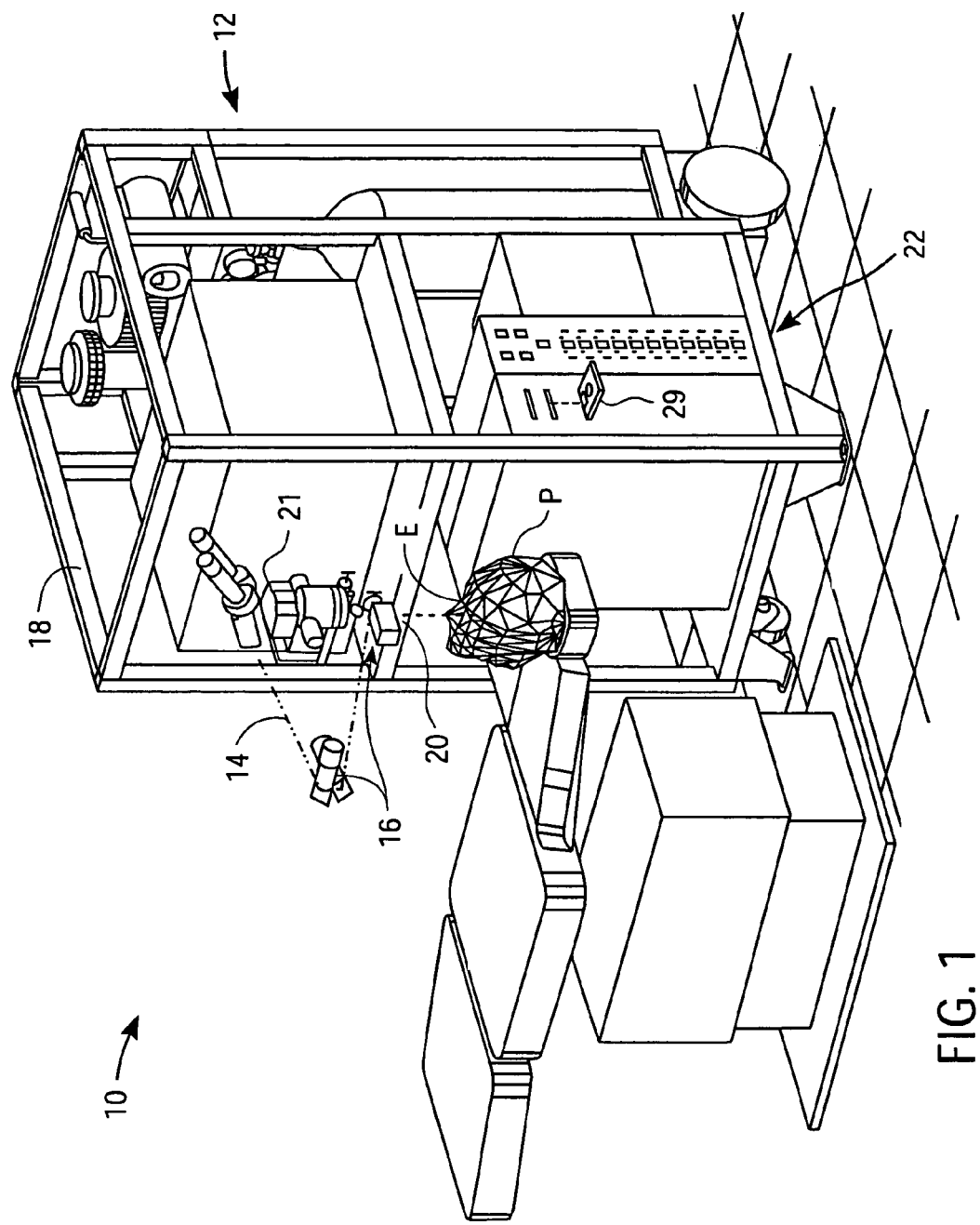
FIG. 1 is a perspective view of a laser ablation system for incorporating the invention.

Referring now to FIG. 1, a laser eye surgery system 10 for incorporating the present invention includes a laser 12 that produces a laser beam 14. Laser 12 is optically coupled to laser delivery optics 16, which directs laser beam 14 to an eye of patient P. A delivery optics support structure (not shown here for clarity) extends from a frame 18 supporting laser 12. An input device 20 is used to align laser system 10 with patient P. A microscope 21 is mounted on the delivery optics support structure, the microscope often being used to image a cornea of eye E. In various embodiments, the laser eye surgery system 10 includes at least some portions of a Star S3 Active Trak™ Excimer Laser System available from VISX, INCORPORATED of Santa Clara, Calif.

While the input device 20 is here schematically illustrated as a joystick, it should be understood that a variety of input mechanisms may be used. Suitable input mechanisms may include trackballs, touch screens, or a wide variety of alternative pointing devices. Still further alternative input mechanisms include keypads, data transmission mechanisms such as an Ethernet, intranet, internet, a modem, or the like.

Laser 12 generally comprises an excimer laser, ideally comprising an argon-fluorine laser producing pulses of laser light having a wavelength of approximately 193 nm. The pulse of laser light typically has a fixed pulse duration having a full width half maximum (FWHM) of about 15 nano seconds during a treatment. Laser 12 will preferably be designed to provide a feedback stabilized fluence at the patient's eye, delivered via delivery optics 16. The present invention may also be useful with alternative sources of ultraviolet or infrared radiation, particularly those adapted to controllably ablate the corneal tissue without causing significant damage to adjacent and/or underlying tissues of the eye. The laser system may include, but is not limited to, excimer lasers such as argon-fluoride excimer lasers (producing laser energy with a wavelength of about 193 nm), solid state lasers, including frequency multiplied solid state lasers such as flash-lamp and diode pumped solid state lasers. Exemplary solid state lasers include UV solid state lasers (approximately 193–215 mm) such as those disclosed in U.S. Pat. Nos. 5,144,630 and 5,742,626; Borsuztky et al., "*Tunable UV Radiation at Short Wavelengths* (188–240 nm) *Generated by Sum Frequency Mixing in Lithium Borate*", *Appl. Phys.* 61:529–532 (1995), and the like. The laser energy may comprise a beam formed as a series of discreet laser pulses. A variety of alternative lasers might also be used. Hence, although an excimer laser is the illustrative source of an ablating beam, other lasers may be used in the present invention.

Laser 12 and delivery optics 16 will generally direct laser beam 14 to the eye E of patient P under the direction of a computer 22. Computer 22 will often selectively adjust laser beam 14 to expose portions of the cornea to the pulses of laser energy so as to effect a predetermined sculpting of the cornea and alter the refractive characteristics of the eye. In many embodiments, both laser 14 and the laser delivery optical system 16 will be under computer control of processor 22 to effect the desired laser sculpting process, with the processor effecting (and optionally modifying) the pattern of laser pulses. The pattern of pulses may by summarized in machine readable data of tangible media 29 in the form of a treatment table, and the treatment table may be adjusted according to feedback input into processor 22 from an automated image analysis system (manually input into the processor by a system operator) in response to feedback data provided from an ablation monitoring system feedback system. Such feedback might be provided by integrating the wavefront measurement system described below with the laser treatment system 10, and processor 22 may continue and/or terminate a sculpting treatment in response to the feedback, and may optionally also modify the planned sculpting based at least in part on the feedback.

Laser beam 14 may be adjusted to produce the desired sculpting using a variety of alternative mechanisms. The laser beam 14 may be selectively limited using one or more variable apertures. An exemplary variable aperture system having a variable iris and a variable width slit is described in U.S. Pat. No. 5,713,892, the full disclosure of which is incorporated herein by reference. The laser beam may also be tailored by varying the size and offset of the laser spot from an axis of the eye, as described in U.S. Pat. No. 5,683,379, and as also described in co-pending U.S. patent application Ser. No. 08/968,380, filed Nov. 12, 1997; and Ser. No. 09/274,999 filed Mar. 22, 1999, the full disclosures of which are incorporated herein by reference.

Still further alternatives are possible, including scanning of the laser beam over a surface of the eye and controlling the number of pulses and/or dwell time at each location, as described, for example, by U.S. Pat. Nos. 4,665,913 (the full disclosure of which is incorporated herein by reference); using masks in the optical path of laser beam 14 which ablate to vary the profile of the beam incident on the cornea, as described in U.S. patent application Ser. No. 08/468,898, filed Jun. 6, 1995 (the full disclosure of which is incorporated herein by reference); hybrid profile-scanning systems in which a variable size beam (typically controlled by a variable width slit and/or variable diameter iris diaphragm) is scanned across the cornea; or the like. The computer programs and control methodology for these laser pattern tailoring techniques are well described in the patent literature.

Additional components and subsystems may be included with laser system 10, as should be understood by those of skill in the art. For example, spatial and/or temporal integrators may be included to control the distribution of energy within the laser beam, as described in U.S. Pat. No. 5,646,791, the disclosure of which is incorporated herein by reference. An ablation effluent evacuator/filter, and other ancillary components of the laser surgery system which are not necessary to an understanding of the invention, need not be described in detail for an understanding of the present invention.

Processor 22 may comprise (or interface with) a conventional PC system including the standard user interface devices such as a keyboard, a display monitor, and the like. Processor 22 will typically include an input device such as a magnetic or optical disk drive, an internet connection, or the like. Such input devices will often be used to download a computer executable code from a tangible storage media 29 embodying any of the methods of the present invention. Tangible storage media 29 may take the form of a floppy disk, an optical disk, a data tape, a volatile or non-volatile memory, or the like, and the processor 22 will include the memory boards and other standard components of modem computer systems for storing and executing this code. Tangible storage media 29 may optionally embody wavefront sensor data, wavefront gradients, a wavefront elevation map, a treatment map, a corneal topography map, a measurement of refraction of the eye, and/or an ablation table.

Figure 1A:
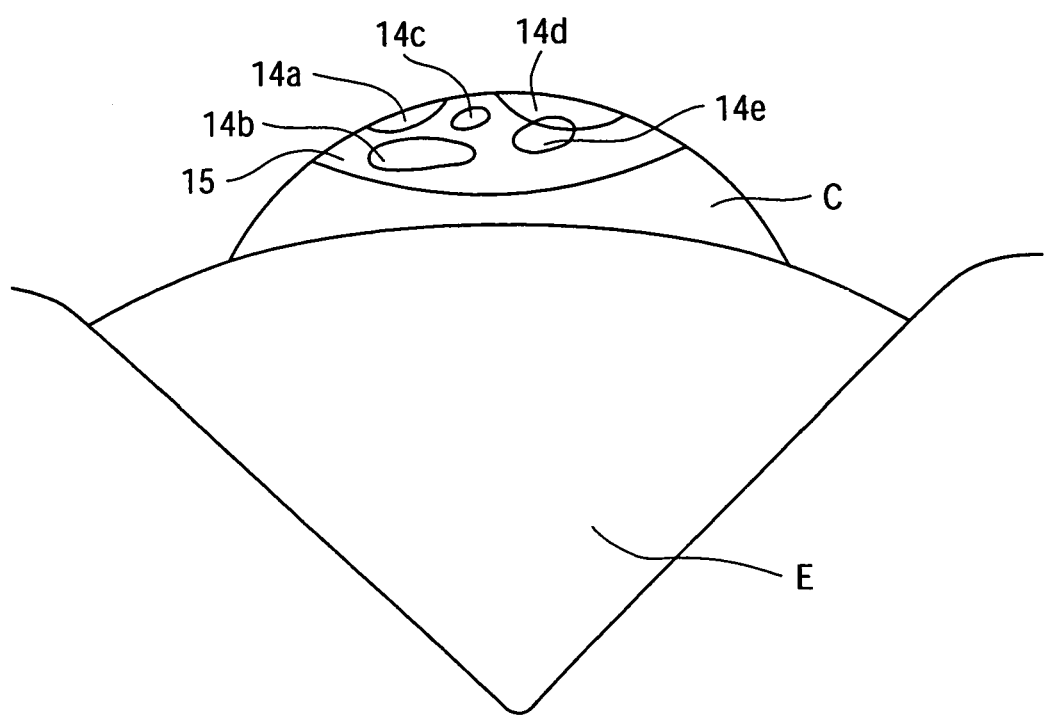
FIG. 1A illustrates an ablation of an eye using a series of scanning laser beam pulses of varying diameter applied over a treatment area of a cornea of an eye.

An ablation of an eye using a series of pulses 14*a*–14*e* of a scanning laser beam is illustrated in FIG. 1A. The series of pulses are applied over a treatment area 15 of a cornea C of an eye E. As illustrated in FIG. 1A pulses 14*e* and 14*d* overlap. A dimension across pulse 14*c* is smaller than a dimension across pulse 14*b*. The series of pulses 14*a* to 14*e* are sequentially applied to eye E.

Figure 2:
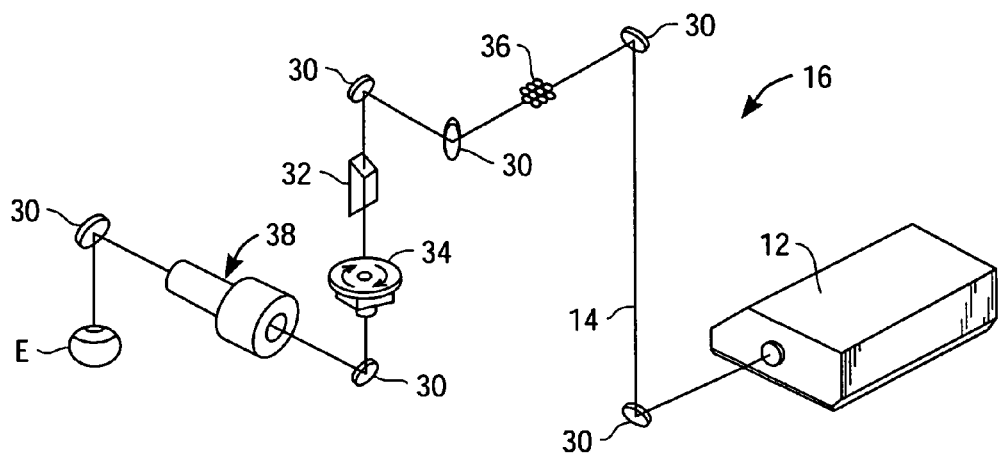
FIGS. 2 and 3 schematically illustrate a laser beam delivery system for selectively directing a laser beam onto the corneal tissue.

Referring now to FIG. 2, laser beam delivery system 16 for directing laser beam 14 at eye E will often include a number of mirrors 30, as well as one or more temporal integrators 32 which may even (or otherwise tailor) the energy distribution across the laser beam. Laser 12 will often comprise an excimer laser as described above.

Figure 3:
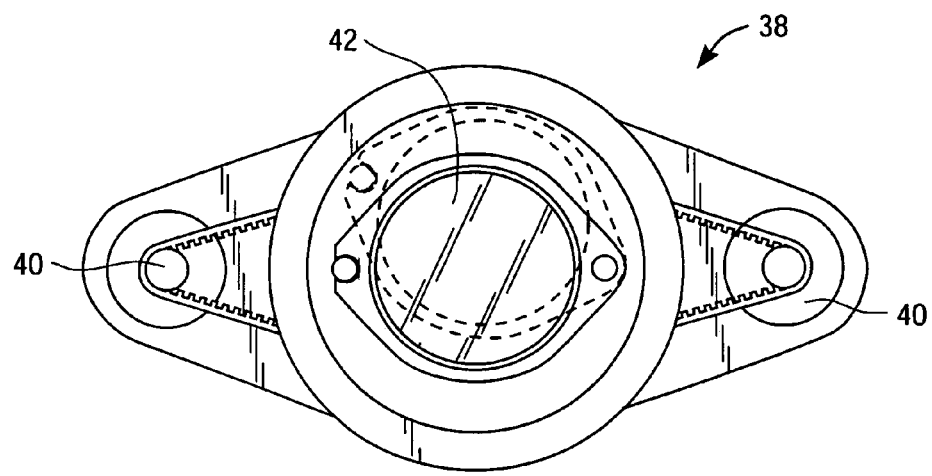

In the exemplary embodiment, a variable aperture 34 changes a diameter and/or slot width to profile laser beam 14, ideally including both a variable diameter iris and a variable width slot. A prism 36 separates laser beam 14 into a plurality of beamlets, which may partially overlap on eye E to smooth edges of the ablation or "crater" from each pulse of the laser beam. Referring now to FIGS. 2 and 3, an offset module 38 includes motors 40 which vary an angular offset of an offset lens 42, and which also change the radial orientation of the offset. Hence, offset module 38 can selectively direct laser beam 14 at a desired lateral region of the cornea. A structure and method for using laser beam delivery system 16 and offset module 38 are more fully described in U.S. Pat. Nos. 6,331,177; 6,203,539; 5,912,775; and 5,646,791 the full disclosures of which are incorporated herein by reference.

Figure 4:
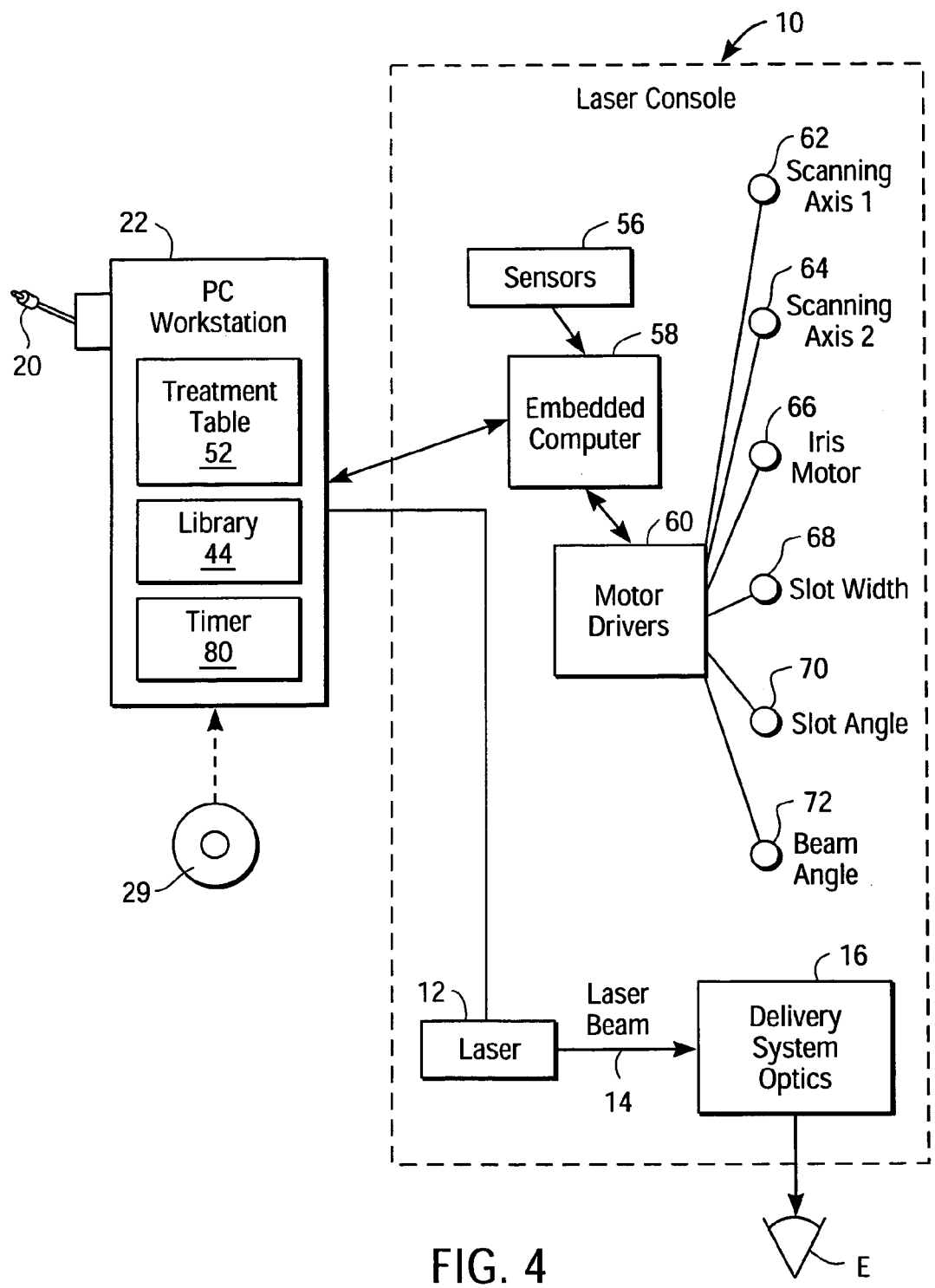
FIG. 4 is a function block diagram illustrating a control architecture of an ablation system as in FIG. 1.

Referring now to FIG. 4, a control system of a laser system 10 is schematically illustrated according to the principles of the present invention. A processor 22 enables precise control of laser system 10 to sculpt a surface shape specified in a laser treatment table 52. A processor 22, which generally comprises a PC workstation, makes use of a computer program stored on a tangible media 29 to generate treatment table 52. Processor 22 includes a library 44 of treatments as described in U.S. Pat. No. 6,245,059, the full disclosure of which is incorporated herein by reference. An embedded computer 58 within laser system 10 is in electronic communication with the PC workstation. Alternatively, a PC workstation may be embedded in the laser system and include an embedded processor card in communication with the PC workstation for directing the ophthalmic surgery.

Embedded computer 58 is in electronic communication with a plurality of sensors 56 and a plurality of motor drivers 60. The motor drivers 60 are coupled to the embedded computer 58 to vary the position and configuration of many of the optical components of the delivery optics 16 according to treatment table 52. For example, first and second scanning axis 62, 64 control the position of the offset lens to move the beamlets over the surface of the cornea. Iris motor 66 controls the diameter of the overall beam, and in some cases, the length of light transmitted through a variable width slot. Similarly slot width driver 68 controls the width of the variable slot. Slot angle driver 70 controls rotation of the slot about its axis. Beam angle driver 72 controls rotation of the beam as effected by a temporal integrator as described above. Processor 22 issues a command for laser 12 to generate a pulse of the laser beam 14 after the various optical elements have been positioned to create a desired crater on eye E. Treatment table 52 comprises a listing of all of the desired craters to be combined so as to effect a treatment therapy.

A timer 80 is located on an add on card of processor 22 and is a Lab-PC-1200 model card having timers 8253/8254. The Lab-PC-1200 model card is available from National Instruments of Austin, Tex. In alternate embodiments, timer 50 is located externally to processor 22. The timer 80 is controlled by a computer program of processor 22 and is adapted to measure time intervals. The laser 12 is electronically coupled to processor 22. Laser 12 fires upon a command issued from processor 22 in response to a time interval measured by timer 80. Processor 22 varies the rate at which laser 62 fires during at least a portion of a treatment of an eye E.

Figure 5:
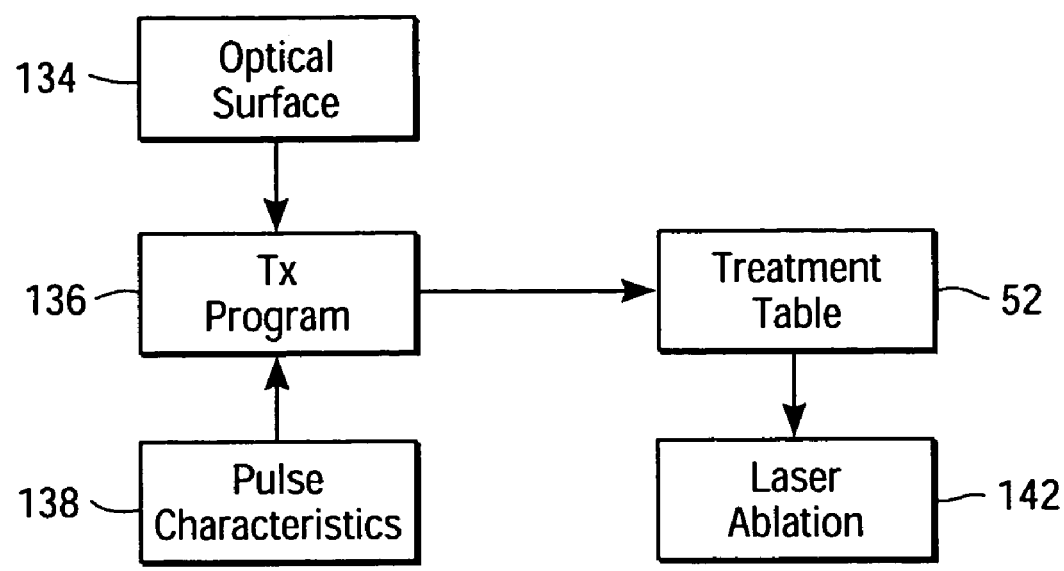
FIG. 5 is a flow chart schematically illustrating a method for determining a corneal ablation treatment program.

A flow chart schematically illustrating a method for determining a corneal ablation treatment program is illustrated in FIG. 5. A treatment program 136 may be calculated from an optical surface 134 so as to remove the regular (spherical and/or cylindrical) and irregular errors of the optical tissues. Methods and systems for determining optical surface 134 are described in U.S. Pat. Nos. 5,163,934 and 6,271,914, the full disclosures of which are herein incorporated by reference. By combining the treatment program 136 with laser ablation pulse characteristics 138 of a particular laser system, a treatment table 52 of ablation pulse locations, sizes, shapes, and/or numbers can be developed. An exemplary method and system for preparing such an ablation table is described in co-pending U.S. patent application No. 60/189,633 filed on Mar. 14, 2000 and entitled "Generating Scanning Spot Locations for Laser Eye Surgery," the full disclosure of which is incorporated herein by reference. Treatment table 52 may optionally be optimized by sorting of the individual pulses so as to avoid localized heating, minimize irregular ablations if the treatment program is interrupted, and the like. Preferably, a treatment table is sorted to apply small diameter pulses to an eye initially followed by large diameter pulses. Alternatively, a treatment table may be sorted to apply large diameter pulses to an eye initially followed by smaller diameter pulses, and an order of pulses may even have a random size distribution. The eye can then be ablated according to the treatment table 52 by laser ablation 142.

Referring now to FIG. 6, several listings from an exemplary laser treatment table 140 are illustrated. A complete treatment table including several hundred pulses is shown in Appendix I. A Patient Name 150, patient identification number (Patient ID) 154, and treated Eye 156 are listed in table 140. A repetition rate (rep rate) 152 is also listed. As shown in FIG. 2B repetition rate 152 is selected to be variable. A refraction 158 having a sphere of −3 D, a cylinder of −2.25D, an axis of 60 degrees and a vertex distance of 0 mm is listed in FIG. 6. A pulse count 160 as listed in FIG. 6 illustrates a total number of 1079 pulses applied during a treatment. Additional fields of treatment table 140 are pulse number 170, iris diameter 172, slit width 174, slit axis 176, X coordinate 178, Y coordinate 180 and delay 182.

For each pulse of treatment table 140, the pulse number 170, iris diameter 172, slit width 174, slit axis 176, X coordinate 178, Y coordinate 180 and delay 182 are listed. The X coordinate 178 and Y coordinate 180 list the X and Y coordinates of the center of each pulse on the cornea relative to a treatment center during a treatment as described above. The iris diameter field 172 lists the dimension across a circular diaphragm opening as projected onto the eye in mun for each pulse during treatment as described above. The slit width 174 and slit axis fields 176 list the dimension across a variable width slot opening as projected onto the eye in mm, and the angle of the slot opening with respect to the eye in degrees as described above. A laser treatment table for scanning a variable width slot is described in U.S. Pat. No. 6,203,539, the full disclosure of which is incorporated herein by reference. The delay 182 lists the delay in ms to the next pulse of the treatment. The firing rate 208 of the laser is the inverse of the delay 206. As shown in FIG. 6, the delay is 50 ms for each pulse which produces a 20 Hz firing rate of laser system 10. For a complete treatment as shown in Appendix I, the delay varies from 125 to 50 ms, and the cross sectional dimension of the beam varies from 1.5 mm to 6.5 mm.

For each pulse diameter and pulse energy applied to the eye, a delay until the next pulse is illustratively summarized in FIG. 7. A delay 206 is listed for each beam diameter 202. A diameter of an iris in mm 202 provides a beam at the surface of the eye having a cross sectional area 204. For an average fluence 210 for each pulse of 160 mJ/cm2, an energy 212 applied to the eye with a pulse of the laser beam is equal to the product of the area 204 and fluence 210. For each diameter 202 listed, the power 214 applied to the eye is the product of the energy applied to the eye with each pulse 212 and the firing rate 208 in Hertz of the laser. For example, for a 5 mm beam diameter the cross sectional area the beam is 0.196 $cm^2$ and the energy applied to the eye is 31.4 mJ with each pulse. The firing rate 208 of the laser 12 is 12.99 Hz and the power 214 applied to the eye is 407.8 mW.

As shown in FIG. 7, the firing rate of the laser is constant for a first portion of a treatment having pulses from 0.5 to 4 mm and variable for a second portion of the treatment having pulses from 4 mm to 6.5 mm. The laser firing rate is preferably limited to improve system reliability and prevent system heating. For example, as shown in FIG. 3A, the laser firing rate is limited to 20 Hz.

A laser firing rate of laser system 10 may vary from the values listed in a treatment table. For example, a closed loop system measures a position of several moving elements as described above, and delays firing of the laser system until each of the several moving elements are positioned. Should a delay in positioning of at least one moving element occur, the laser pulse is delayed until the element is correctly positioned. Also, an eye tracking system may delay a pulse of a treatment in response to a rapidly moving eye or an eye that has temporarily moved beyond a limit, for example an eye with a nystagmus.

Firing rates for a laser having a nearly constant power of 400 mW applied to an eye are illustrated in FIG. 8 for a treatment using different amounts of energy with several pulses of a laser beam. Any power level, range of beam diameters and range of firing rates can be selected to deliver a desired amount of optical power to eye E of patient P. As illustrated in FIG. 8 a beam diameter 202 of 3 mm at the eye provides a per pulse energy 212 of 11.3 mJ for an average fluence 210 of 160 mJ/cm$^2$. To provide a power 214 of 400 mW to the eye, a firing rate of 35 Hz is used during treatment. For a beam diameter 202 of 1 mm having a per pulse energy 212 of 1.26 mJ, a firing rate of 318 Hz is used. A range of beam diameters is from about 1 to 3 mm and a firing rate of the laser is from about 35 Hz to 318 Hz.

While the above provides a complete and accurate description of specific embodiments of the invention, several changes and adaptations of the present invention may be readily made. For example, although specific reference has been made to a laser beam of varying size, a varying firing rate may be used during treatment with a pulsed laser providing a fixed beam diameter and a varying amount of energy delivered to a treatment area among pulses of the beam. Also, while treatments using several beam diameters have been described, a variable laser firing rate during treatment may be desirable with treatments using only two sizes of a laser beam. Therefore, the scope of the invention is limited solely by the following claims.

APPENDIX I

| Patient Name | | | | | |
|---|---|---|---|---|---|
| reprate | variable | | | | |
| Patient ID | | | | | |
| Eye | OD | | | | |
| Refraction | −3 | −2.25 | 60 | 0 | |
| Pulse Count | 1079 | | | | |

| Pulse No. | Iris Diam | Slit Width | Slit Axis | X (mm) | Y (mm) | Delay (ms) |
|---|---|---|---|---|---|---|
| 1 | 1.5 | 6.5 | 0 | −0.4 | 0.2 | 50 |
| 2 | 1.5 | 6.5 | 0 | 0.3 | −0.6 | 50 |
| 3 | 1.5 | 6.5 | 0 | −0.1 | 0 | 50 |
| 4 | 1.5 | 6.5 | 0 | 0.2 | 1 | 50 |
| 5 | 1.5 | 6.5 | 0 | −0.3 | −0.8 | 50 |
| 6 | 1.5 | 6.5 | 0 | 1.7 | 0.1 | 50 |
| 7 | 1.5 | 6.5 | 0 | 0.6 | −1.5 | 50 |
| 8 | 1.5 | 6.5 | 0 | −0.6 | −2.1 | 50 |
| 9 | 1.5 | 6.5 | 0 | 0.3 | 2.6 | 50 |
| 10 | 1.5 | 6.5 | 0 | 1 | 2.4 | 50 |
| 11 | 1.5 | 6.5 | 0 | 2 | 1.7 | 50 |
| 12 | 1.5 | 6.5 | 0 | 2.7 | −0.1 | 50 |
| 13 | 1.5 | 6.5 | 0 | −0.3 | −2.6 | 50 |
| 14 | 1.5 | 6.5 | 0 | −1.9 | −1.8 | 50 |
| 15 | 1.5 | 6.5 | 0 | −2.8 | 0.4 | 50 |
| 16 | 1.5 | 6.5 | 0 | −2.8 | 1 | 50 |
| 17 | 1.5 | 6.5 | 0 | −2.7 | 1 | 50 |
| 18 | 1.5 | 6.5 | 0 | −2.6 | 1.5 | 50 |
| 19 | 1.5 | 6.5 | 0 | −2.4 | 1.7 | 50 |
| 20 | 1.5 | 6.5 | 0 | −1.8 | 2.4 | 50 |
| 21 | 1.5 | 6.5 | 0 | −0.2 | 3 | 50 |
| 22 | 1.5 | 6.5 | 0 | 2.8 | 0.9 | 50 |
| 23 | 1.5 | 6.5 | 0 | 3 | 0 | 50 |
| 24 | 1.5 | 6.5 | 0 | 2.9 | −0.5 | 50 |
| 25 | 1.5 | 6.5 | 0 | 2.6 | −1.2 | 50 |
| 26 | 1.5 | 6.5 | 0 | 2.3 | −1.6 | 50 |
| 27 | 1.5 | 6.5 | 0 | 2.3 | −1.8 | 50 |
| 28 | 1.5 | 6.5 | 0 | 2.2 | −2 | 50 |
| 29 | 1.5 | 6.5 | 0 | 2 | −2 | 50 |
| 30 | 1.5 | 6.5 | 0 | −1.5 | −2.5 | 50 |
| 31 | 1.5 | 6.5 | 0 | −1.9 | −2 | 50 |
| 32 | 1.5 | 6.5 | 0 | −2.2 | −1.6 | 50 |
| 33 | 1.5 | 6.5 | 0 | −2.8 | −1.1 | 50 |
| 34 | 1.5 | 6.5 | 0 | −2.7 | −0.7 | 50 |
| 35 | 1.5 | 6.5 | 0 | −3.4 | 0.1 | 50 |
| 36 | 1.5 | 6.5 | 0 | −3.2 | 0.1 | 50 |
| 37 | 1.5 | 6.5 | 0 | −3.6 | 0.2 | 50 |
| 38 | 1.5 | 6.5 | 0 | −3.1 | 0.2 | 50 |
| 39 | 1.5 | 6.5 | 0 | −3.5 | 0.3 | 50 |
| 40 | 1.5 | 6.5 | 0 | −3 | 0.3 | 50 |
| 41 | 1.5 | 6.5 | 0 | −3 | 0.3 | 50 |
| 42 | 1.5 | 6.5 | 0 | −3.4 | 0.4 | 50 |
| 43 | 1.5 | 6.5 | 0 | −3.1 | 0.4 | 50 |
| 44 | 1.5 | 6.5 | 0 | −3.4 | 0.5 | 50 |
| 45 | 1.5 | 6.5 | 0 | −3.4 | 0.6 | 50 |
| 46 | 1.5 | 6.5 | 0 | −3.3 | 0.6 | 50 |
| 47 | 1.5 | 6.5 | 0 | −3.3 | 0.6 | 50 |
| 48 | 1.5 | 6.5 | 0 | −3 | 0.6 | 50 |
| 49 | 1.5 | 6.5 | 0 | −3.3 | 0.7 | 50 |
| 50 | 1.5 | 6.5 | 0 | −3.2 | 0.7 | 50 |
| 51 | 1.5 | 6.5 | 0 | −3.2 | 0.7 | 50 |
| 52 | 1.5 | 6.5 | 0 | −3.5 | 0.8 | 50 |
| 53 | 1.5 | 6.5 | 0 | −3.4 | 0.8 | 50 |
| 54 | 1.5 | 6.5 | 0 | −3.3 | 0.8 | 50 |
| 55 | 1.5 | 6.5 | 0 | −3.1 | 0.8 | 50 |
| 56 | 1.5 | 6.5 | 0 | −3 | 0.8 | 50 |
| 57 | 1.5 | 6.5 | 0 | −3.2 | 1 | 50 |
| 58 | 1.5 | 6.5 | 0 | −3.4 | 1.1 | 50 |
| 59 | 1.5 | 6.5 | 0 | −3.3 | 1.1 | 50 |
| 60 | 1.5 | 6.5 | 0 | −3.3 | 1.1 | 50 |
| 61 | 1.5 | 6.5 | 0 | −3.2 | 1.1 | 50 |
| 62 | 1.5 | 6.5 | 0 | −3.2 | 1.2 | 50 |
| 63 | 1.5 | 6.5 | 0 | −3.3 | 1.3 | 50 |
| 64 | 1.5 | 6.5 | 0 | −3.3 | 1.3 | 50 |
| 65 | 1.5 | 6.5 | 0 | −3.2 | 1.4 | 50 |
| 66 | 1.5 | 6.5 | 0 | −3.1 | 1.4 | 50 |
| 67 | 1.5 | 6.5 | 0 | −2.8 | 1.3 | 50 |
| 68 | 1.5 | 6.5 | 0 | −2.9 | 1.4 | 50 |
| 69 | 1.5 | 6.5 | 0 | −3.1 | 1.5 | 50 |
| 70 | 1.5 | 6.5 | 0 | −3.2 | 1.6 | 50 |
| 71 | 1.5 | 6.5 | 0 | −2.9 | 1.5 | 50 |
| 72 | 1.5 | 6.5 | 0 | −2.7 | 1.4 | 50 |
| 73 | 1.5 | 6.5 | 0 | −3.2 | 1.7 | 50 |
| 74 | 1.5 | 6.5 | 0 | −3 | 1.6 | 50 |
| 75 | 1.5 | 6.5 | 0 | −2.7 | 1.5 | 50 |
| 76 | 1.5 | 6.5 | 0 | −3 | 1.8 | 50 |
| 77 | 1.5 | 6.5 | 0 | −2.9 | 1.8 | 50 |
| 78 | 1.5 | 6.5 | 0 | −2.9 | 1.8 | 50 |
| 79 | 1.5 | 6.5 | 0 | −3 | 1.9 | 50 |
| 80 | 1.5 | 6.5 | 0 | −3 | 1.9 | 50 |
| 81 | 1.5 | 6.5 | 0 | −2.8 | 1.8 | 50 |
| 82 | 1.5 | 6.5 | 0 | −2.6 | 1.7 | 50 |
| 83 | 1.5 | 6.5 | 0 | −2.9 | 1.9 | 50 |
| 84 | 1.5 | 6.5 | 0 | −2.9 | 1.9 | 50 |
| 85 | 1.5 | 6.5 | 0 | −2.9 | 2 | 50 |
| 86 | 1.5 | 6.5 | 0 | −2.9 | 2.1 | 50 |
| 87 | 1.5 | 6.5 | 0 | −2.9 | 2.1 | 50 |
| 88 | 1.5 | 6.5 | 0 | −2.6 | 1.9 | 50 |
| 89 | 1.5 | 6.5 | 0 | −2.7 | 2 | 50 |
| 90 | 1.5 | 6.5 | 0 | −2.7 | 2 | 50 |
| 91 | 1.5 | 6.5 | 0 | −2.6 | 2.1 | 50 |
| 92 | 1.5 | 6.5 | 0 | −2.8 | 2.3 | 50 |
| 93 | 1.5 | 6.5 | 0 | −2.4 | 2 | 50 |
| 94 | 1.5 | 6.5 | 0 | −2.6 | 2.2 | 50 |
| 95 | 1.5 | 6.5 | 0 | −2.7 | 2.3 | 50 |
| 96 | 1.5 | 6.5 | 0 | −2.7 | 2.3 | 50 |
| 97 | 1.5 | 6.5 | 0 | −2.4 | 2.1 | 50 |
| 98 | 1.5 | 6.5 | 0 | −2.5 | 2.2 | 50 |
| 99 | 1.5 | 6.5 | 0 | −2.5 | 2.3 | 50 |
| 100 | 1.5 | 6.5 | 0 | −2.6 | 2.4 | 50 |
| 101 | 1.5 | 6.5 | 0 | −2.4 | 2.3 | 50 |
| 102 | 1.5 | 6.5 | 0 | −2.4 | 2.4 | 50 |
| 103 | 1.5 | 6.5 | 0 | −2.3 | 2.4 | 50 |
| 104 | 1.5 | 6.5 | 0 | −2.4 | 2.6 | 50 |
| 105 | 1.5 | 6.5 | 0 | −2.3 | 2.5 | 50 |
| 106 | 1.5 | 6.5 | 0 | −2.3 | 2.5 | 50 |
| 107 | 1.5 | 6.5 | 0 | −2.3 | 2.6 | 50 |
| 108 | 1.5 | 6.5 | 0 | −2.2 | 2.5 | 50 |
| 109 | 1.5 | 6.5 | 0 | −2.2 | 2.6 | 50 |

APPENDIX I-continued

| | | | | | | |
|---|---|---|---|---|---|---|
| 110 | 1.5 | 6.5 | 0 | −2.2 | 2.6 | 50 |
| 111 | 1.5 | 6.5 | 0 | −2.2 | 2.7 | 50 |
| 112 | 1.5 | 6.5 | 0 | −2.1 | 2.6 | 50 |
| 113 | 1.5 | 6.5 | 0 | −2.1 | 2.6 | 50 |
| 114 | 1.5 | 6.5 | 0 | −2.2 | 3 | 50 |
| 115 | 1.5 | 6.5 | 0 | −2.1 | 2.9 | 50 |
| 116 | 1.5 | 6.5 | 0 | −2 | 2.9 | 50 |
| 117 | 1.5 | 6.5 | 0 | −1.9 | 2.8 | 50 |
| 118 | 1.5 | 6.5 | 0 | −1.8 | 2.7 | 50 |
| 119 | 1.5 | 6.5 | 0 | −1.9 | 2.9 | 50 |
| 120 | 1.5 | 6.5 | 0 | −1.8 | 2.8 | 50 |
| 121 | 1.5 | 6.5 | 0 | −1.9 | 3 | 50 |
| 122 | 1.5 | 6.5 | 0 | −1.6 | 2.6 | 50 |
| 123 | 1.5 | 6.5 | 0 | −1.9 | 3.1 | 50 |
| 124 | 1.5 | 6.5 | 0 | −1.7 | 2.8 | 50 |
| 125 | 1.5 | 6.5 | 0 | −1.8 | 3.1 | 50 |
| 126 | 1.5 | 6.5 | 0 | −1.6 | 3 | 50 |
| 127 | 1.5 | 6.5 | 0 | −1.4 | 2.8 | 50 |
| 128 | 1.5 | 6.5 | 0 | −1.5 | 3 | 50 |
| 129 | 1.5 | 6.5 | 0 | −1.7 | 3.5 | 50 |
| 130 | 1.5 | 6.5 | 0 | −1.5 | 3.2 | 50 |
| 131 | 1.5 | 6.5 | 0 | −1.3 | 2.9 | 50 |
| 132 | 1.5 | 6.5 | 0 | −1.3 | 2.9 | 50 |
| 133 | 1.5 | 6.5 | 0 | −1.4 | 3.2 | 50 |
| 134 | 1.5 | 6.5 | 0 | −1.4 | 3.3 | 50 |
| 135 | 1.5 | 6.5 | 0 | −1.4 | 3.4 | 50 |
| 136 | 1.5 | 6.5 | 0 | −1.3 | 3.2 | 50 |
| 137 | 1.5 | 6.5 | 0 | −1.3 | 3.3 | 50 |
| 138 | 1.5 | 6.5 | 0 | −1.2 | 3.2 | 50 |
| 139 | 1.5 | 6.5 | 0 | −1.2 | 3.3 | 50 |
| 140 | 1.5 | 6.5 | 0 | −1.1 | 3.2 | 50 |
| 141 | 1.5 | 6.5 | 0 | −1 | 3.2 | 50 |
| 142 | 1.5 | 6.5 | 0 | −0.9 | 2.9 | 50 |
| 143 | 1.5 | 6.5 | 0 | −1.1 | 3.6 | 50 |
| 144 | 1.5 | 6.5 | 0 | −1 | 3.4 | 50 |
| 145 | 1.5 | 6.5 | 0 | −0.9 | 3.2 | 50 |
| 146 | 1.5 | 6.5 | 0 | −0.9 | 3.5 | 50 |
| 147 | 1.5 | 6.5 | 0 | −0.8 | 3.2 | 50 |
| 148 | 1.5 | 6.5 | 0 | −0.8 | 3.3 | 50 |
| 149 | 1.5 | 6.5 | 0 | −0.7 | 3.4 | 50 |
| 150 | 1.5 | 6.5 | 0 | −0.6 | 3.4 | 50 |
| 151 | 1.5 | 6.5 | 0 | −0.6 | 3.6 | 50 |
| 152 | 1.5 | 6.5 | 0 | −0.5 | 3.6 | 50 |
| 153 | 1.5 | 6.5 | 0 | −0.3 | 3.2 | 50 |
| 154 | 1.5 | 6.5 | 0 | −0.3 | 3.6 | 50 |
| 155 | 1.5 | 6.5 | 0 | −0.1 | 3.1 | 50 |
| 156 | 1.5 | 6.5 | 0 | −0.1 | 3.3 | 50 |
| 157 | 1.5 | 6.5 | 0 | 0 | 3.8 | 50 |
| 158 | 1.5 | 6.5 | 0 | 0 | 3.6 | 50 |
| 159 | 1.5 | 6.5 | 0 | 0.1 | 3.9 | 50 |
| 160 | 1.5 | 6.5 | 0 | 0.2 | 3.2 | 50 |
| 161 | 1.5 | 6.5 | 0 | 0.2 | 3.1 | 50 |
| 162 | 1.5 | 6.5 | 0 | 0.4 | 3.9 | 50 |
| 163 | 1.5 | 6.5 | 0 | 0.5 | 3.6 | 50 |
| 164 | 1.5 | 6.5 | 0 | 0.6 | 3.9 | 50 |
| 165 | 1.5 | 6.5 | 0 | 0.6 | 3.9 | 50 |
| 166 | 1.5 | 6.5 | 0 | 0.8 | 3.7 | 50 |
| 167 | 1.5 | 6.5 | 0 | 0.9 | 3.6 | 50 |
| 168 | 1.5 | 6.5 | 0 | 1 | 3.9 | 50 |
| 169 | 1.5 | 6.5 | 0 | 1.1 | 3.8 | 50 |
| 170 | 1.5 | 6.5 | 0 | 1 | 2.9 | 50 |
| 171 | 1.5 | 6.5 | 0 | 1.3 | 3.5 | 50 |
| 172 | 1.5 | 6.5 | 0 | 1.2 | 3.1 | 50 |
| 173 | 1.5 | 6.5 | 0 | 1.5 | 3.2 | 50 |
| 174 | 1.5 | 6.5 | 0 | 1.5 | 3.1 | 50 |
| 175 | 1.5 | 6.5 | 0 | 2.6 | 1.9 | 50 |
| 176 | 1.5 | 6.5 | 0 | 3.1 | 1.9 | 50 |
| 177 | 1.5 | 6.5 | 0 | 3 | 1.6 | 50 |
| 178 | 1.5 | 6.5 | 0 | 2.7 | 1.4 | 50 |
| 179 | 1.5 | 6.5 | 0 | 3.1 | 1.4 | 50 |
| 180 | 1.5 | 6.5 | 0 | 2.8 | 1.2 | 50 |
| 181 | 1.5 | 6.5 | 0 | 3.3 | 1.2 | 50 |
| 182 | 1.5 | 6.5 | 0 | 3.1 | 1 | 50 |
| 183 | 1.5 | 6.5 | 0 | 3.4 | 1 | 50 |
| 184 | 1.5 | 6.5 | 0 | 3.3 | 0.8 | 50 |
| 185 | 1.5 | 6.5 | 0 | 3.4 | 0.8 | 50 |
| 186 | 1.5 | 6.5 | 0 | 3.2 | 0.7 | 50 |
| 187 | 1.5 | 6.5 | 0 | 3.1 | 0.6 | 50 |
| 188 | 1.5 | 6.5 | 0 | 3.4 | 0.6 | 50 |
| 189 | 1.5 | 6.5 | 0 | 3.6 | 0.5 | 50 |
| 190 | 1.5 | 6.5 | 0 | 3.2 | 0.4 | 50 |
| 191 | 1.5 | 6.5 | 0 | 3.3 | 0.3 | 50 |
| 192 | 1.5 | 6.5 | 0 | 3.5 | 0.3 | 50 |
| 193 | 1.5 | 6.5 | 0 | 3.1 | 0.2 | 50 |
| 194 | 1.5 | 6.5 | 0 | 3.2 | 0.2 | 50 |
| 195 | 1.5 | 6.5 | 0 | 3.4 | 0.1 | 50 |
| 196 | 1.5 | 6.5 | 0 | 3.5 | 0.1 | 50 |
| 197 | 1.5 | 6.5 | 0 | 3.3 | 0 | 50 |
| 198 | 1.5 | 6.5 | 0 | 3.6 | 0 | 50 |
| 199 | 1.5 | 6.5 | 0 | 3.6 | 0 | 50 |
| 200 | 1.5 | 6.5 | 0 | 3.3 | 0 | 50 |
| 201 | 1.5 | 6.5 | 0 | 3.4 | −0.1 | 50 |
| 202 | 1.5 | 6.5 | 0 | 3.5 | −0.4 | 50 |
| 203 | 1.5 | 6.5 | 0 | 3.5 | −0.4 | 50 |
| 204 | 1.5 | 6.5 | 0 | 3.1 | −0.4 | 50 |
| 205 | 1.5 | 6.5 | 0 | 3 | −0.4 | 50 |
| 206 | 1.5 | 6.5 | 0 | 3.6 | −0.5 | 50 |
| 207 | 1.5 | 6.5 | 0 | 3.4 | −0.5 | 50 |
| 208 | 1.5 | 6.5 | 0 | 3.1 | −0.7 | 50 |
| 209 | 1.5 | 6.5 | 0 | 3 | −0.7 | 50 |
| 210 | 1.5 | 6.5 | 0 | 3.4 | −0.8 | 50 |
| 211 | 1.5 | 6.5 | 0 | 3.3 | −0.8 | 50 |
| 212 | 1.5 | 6.5 | 0 | 3.1 | −0.8 | 50 |
| 213 | 1.5 | 6.5 | 0 | 3 | −0.8 | 50 |
| 214 | 1.5 | 6.5 | 0 | 3.3 | −0.9 | 50 |
| 215 | 1.5 | 6.5 | 0 | 3.3 | −0.9 | 50 |
| 216 | 1.5 | 6.5 | 0 | 3.4 | −1 | 50 |
| 217 | 1.5 | 6.5 | 0 | 2.9 | −0.9 | 50 |
| 218 | 1.5 | 6.5 | 0 | 3.3 | −1.1 | 50 |
| 219 | 1.5 | 6.5 | 0 | 3.3 | −1.1 | 50 |
| 220 | 1.5 | 6.5 | 0 | 3.1 | −1.1 | 50 |
| 221 | 1.5 | 6.5 | 0 | 3.2 | −1.2 | 50 |
| 222 | 1.5 | 6.5 | 0 | 3.2 | −1.2 | 50 |
| 223 | 1.5 | 6.5 | 0 | 3.3 | −1.3 | 50 |
| 224 | 1.5 | 6.5 | 0 | 3 | −1.2 | 50 |
| 225 | 1.5 | 6.5 | 0 | 3.2 | −1.3 | 50 |
| 226 | 1.5 | 6.5 | 0 | 3 | −1.4 | 50 |
| 227 | 1.5 | 6.5 | 0 | 2.9 | −1.4 | 50 |
| 228 | 1.5 | 6.5 | 0 | 3.1 | −1.5 | 50 |
| 229 | 1.5 | 6.5 | 0 | 3.3 | −1.6 | 50 |
| 230 | 1.5 | 6.5 | 0 | 2.9 | −1.5 | 50 |
| 231 | 1.5 | 6.5 | 0 | 2.9 | −1.5 | 50 |
| 232 | 1.5 | 6.5 | 0 | 3 | −1.6 | 50 |
| 233 | 1.5 | 6.5 | 0 | 3.1 | −1.7 | 50 |
| 234 | 1.5 | 6.5 | 0 | 3 | −1.7 | 50 |
| 235 | 1.5 | 6.5 | 0 | 3.1 | −1.8 | 50 |
| 236 | 1.5 | 6.5 | 0 | 2.7 | −1.6 | 50 |
| 237 | 1.5 | 6.5 | 0 | 3 | −1.8 | 50 |
| 238 | 1.5 | 6.5 | 0 | 3 | −1.8 | 50 |
| 239 | 1.5 | 6.5 | 0 | 3 | −1.8 | 50 |
| 240 | 1.5 | 6.5 | 0 | 2.8 | −1.7 | 50 |
| 241 | 1.5 | 6.5 | 0 | 2.8 | −1.7 | 50 |
| 242 | 1.5 | 6.5 | 0 | 2.9 | −1.8 | 50 |
| 243 | 1.5 | 6.5 | 0 | 2.7 | −1.7 | 50 |
| 244 | 1.5 | 6.5 | 0 | 3 | −1.9 | 50 |
| 245 | 1.5 | 6.5 | 0 | 2.9 | −2.1 | 50 |
| 246 | 1.5 | 6.5 | 0 | 2.6 | −1.9 | 50 |
| 247 | 1.5 | 6.5 | 0 | 2.7 | −2 | 50 |
| 248 | 1.5 | 6.5 | 0 | 2.8 | −2.1 | 50 |
| 249 | 1.5 | 6.5 | 0 | 2.6 | −2 | 50 |
| 250 | 1.5 | 6.5 | 0 | 2.7 | −2.1 | 50 |
| 251 | 1.5 | 6.5 | 0 | 2.8 | −2.2 | 50 |
| 252 | 1.5 | 6.5 | 0 | 2.6 | −2.1 | 50 |
| 253 | 1.5 | 6.5 | 0 | 2.4 | −2 | 50 |
| 254 | 1.5 | 6.5 | 0 | 2.4 | −2 | 50 |
| 255 | 1.5 | 6.5 | 0 | 2.4 | −2.1 | 50 |
| 256 | 1.5 | 6.5 | 0 | 2.5 | −2.2 | 50 |
| 257 | 1.5 | 6.5 | 0 | 2.6 | −2.3 | 50 |
| 258 | 1.5 | 6.5 | 0 | 2.6 | −2.3 | 50 |
| 259 | 1.5 | 6.5 | 0 | 2.7 | −2.4 | 50 |
| 260 | 1.5 | 6.5 | 0 | 2.4 | −2.2 | 50 |
| 261 | 1.5 | 6.5 | 0 | 2.5 | −2.3 | 50 |
| 262 | 1.5 | 6.5 | 0 | 2.4 | −2.3 | 50 |
| 263 | 1.5 | 6.5 | 0 | 2.5 | −2.4 | 50 |
| 264 | 1.5 | 6.5 | 0 | 2.4 | −2.5 | 50 |
| 265 | 1.5 | 6.5 | 0 | 2.3 | −2.4 | 50 |
| 266 | 1.5 | 6.5 | 0 | 2.2 | −2.3 | 50 |
| 267 | 1.5 | 6.5 | 0 | 2.2 | −2.4 | 50 |

APPENDIX I-continued

| | | | | | | |
|---|---|---|---|---|---|---|
| 268 | 1.5 | 6.5 | 0 | 2.1 | −2.3 | 50 |
| 269 | 1.5 | 6.5 | 0 | 2.3 | −2.6 | 50 |
| 270 | 1.5 | 6.5 | 0 | 2.2 | −2.5 | 50 |
| 271 | 1.5 | 6.5 | 0 | 2.1 | −2.5 | 50 |
| 272 | 1.5 | 6.5 | 0 | 2.2 | −2.7 | 50 |
| 273 | 1.5 | 6.5 | 0 | 2 | −2.5 | 50 |
| 274 | 1.5 | 6.5 | 0 | 2.3 | −2.9 | 50 |
| 275 | 1.5 | 6.5 | 0 | 2.2 | −2.8 | 50 |
| 276 | 1.5 | 6.5 | 0 | 2.1 | −2.7 | 50 |
| 277 | 1.5 | 6.5 | 0 | 2 | −2.8 | 50 |
| 278 | 1.5 | 6.5 | 0 | 1.9 | −2.8 | 50 |
| 279 | 1.5 | 6.5 | 0 | 1.9 | −2.8 | 50 |
| 280 | 1.5 | 6.5 | 0 | 2 | −3 | 50 |
| 281 | 1.5 | 6.5 | 0 | 2 | −3 | 50 |
| 282 | 1.5 | 6.5 | 0 | 1.9 | −2.9 | 50 |
| 283 | 1.5 | 6.5 | 0 | 1.8 | −2.8 | 50 |
| 284 | 1.5 | 6.5 | 0 | 1.9 | −3 | 50 |
| 285 | 1.5 | 6.5 | 0 | 1.6 | −2.7 | 50 |
| 286 | 1.5 | 6.5 | 0 | 1.6 | −2.7 | 50 |
| 287 | 1.5 | 6.5 | 0 | 1.8 | −3.1 | 50 |
| 288 | 1.5 | 6.5 | 0 | 1.6 | −2.9 | 50 |
| 289 | 1.5 | 6.5 | 0 | 1.6 | −2.9 | 50 |
| 290 | 1.5 | 6.5 | 0 | 1.5 | −2.8 | 50 |
| 291 | 1.5 | 6.5 | 0 | 1.7 | −3.2 | 50 |
| 292 | 1.5 | 6.5 | 0 | 1.6 | −3.2 | 50 |
| 293 | 1.5 | 6.5 | 0 | 1.4 | −3.1 | 50 |
| 294 | 1.5 | 6.5 | 0 | 1.3 | −2.9 | 50 |
| 295 | 1.5 | 6.5 | 0 | 1.4 | −3.2 | 50 |
| 296 | 1.5 | 6.5 | 0 | 1.4 | −3.3 | 50 |
| 297 | 1.5 | 6.5 | 0 | 1.3 | −3.3 | 50 |
| 298 | 1.5 | 6.5 | 0 | 1.3 | −3.3 | 50 |
| 299 | 1.5 | 6.5 | 0 | 1.1 | −3 | 50 |
| 300 | 1.5 | 6.5 | 0 | 1.1 | −3.7 | 50 |
| 301 | 1.5 | 6.5 | 0 | 0.9 | −3.4 | 50 |
| 302 | 1.5 | 6.5 | 0 | 0.8 | −3.1 | 50 |
| 303 | 1.5 | 6.5 | 0 | 0.9 | −3.5 | 50 |
| 304 | 1.5 | 6.5 | 0 | 0.8 | −3.2 | 50 |
| 305 | 1.5 | 6.5 | 0 | 0.8 | −3.3 | 50 |
| 306 | 1.5 | 6.5 | 0 | 0.8 | −3.4 | 50 |
| 307 | 1.5 | 6.5 | 0 | 0.8 | −3.6 | 50 |
| 308 | 1.5 | 6.5 | 0 | 0.7 | −3.3 | 50 |
| 309 | 1.5 | 6.5 | 0 | 0.8 | −3.9 | 50 |
| 310 | 1.5 | 6.5 | 0 | 0.6 | −3 | 50 |
| 311 | 1.5 | 6.5 | 0 | 0.6 | −3.3 | 50 |
| 312 | 1.5 | 6.5 | 0 | 0.5 | −3.9 | 50 |
| 313 | 1.5 | 6.5 | 0 | 0.4 | −3.3 | 50 |
| 314 | 1.5 | 6.5 | 0 | 0.4 | −3.4 | 50 |
| 315 | 1.5 | 6.5 | 0 | 0.4 | −3.9 | 50 |
| 316 | 1.5 | 6.5 | 0 | 0.3 | −3.5 | 50 |
| 317 | 1.5 | 6.5 | 0 | 0.2 | −3.1 | 50 |
| 318 | 1.5 | 6.5 | 0 | 0.1 | −3.9 | 50 |
| 319 | 1.5 | 6.5 | 0 | −0.2 | −3.8 | 50 |
| 320 | 1.5 | 6.5 | 0 | −0.2 | −3.5 | 50 |
| 321 | 1.5 | 6.5 | 0 | −0.3 | −3.5 | 50 |
| 322 | 1.5 | 6.5 | 0 | −0.3 | −3.4 | 50 |
| 323 | 1.5 | 6.5 | 0 | −0.8 | −3.3 | 50 |
| 324 | 1.5 | 6.5 | 0 | −0.9 | −3.6 | 50 |
| 325 | 1.5 | 6.5 | 0 | −1.1 | −3.8 | 50 |
| 326 | 1.5 | 6.5 | 0 | −1 | −3.2 | 50 |
| 327 | 1.5 | 6.5 | 0 | −1.5 | −3.5 | 50 |
| 328 | 1.5 | 6.5 | 0 | −1.7 | −3.1 | 50 |
| 329 | 1.5 | 6.5 | 0 | −3.3 | −1.9 | 50 |
| 330 | 1.5 | 6.5 | 0 | −2.7 | −1.5 | 50 |
| 331 | 1.5 | 6.5 | 0 | −2.9 | −1.5 | 50 |
| 332 | 1.5 | 6.5 | 0 | −2.9 | −1.3 | 50 |
| 333 | 1.5 | 6.5 | 0 | −3.2 | −1.4 | 50 |
| 334 | 1.5 | 6.5 | 0 | −3.1 | −1.1 | 50 |
| 335 | 1.5 | 6.5 | 0 | −3.5 | −1.2 | 50 |
| 336 | 1.5 | 6.5 | 0 | −2.9 | −0.9 | 50 |
| 337 | 1.5 | 6.5 | 0 | −3.1 | −0.9 | 50 |
| 338 | 1.5 | 6.5 | 0 | −3 | −0.8 | 50 |
| 339 | 1.5 | 6.5 | 0 | −3.2 | −0.7 | 50 |
| 340 | 1.5 | 6.5 | 0 | −3.3 | −0.6 | 50 |
| 341 | 1.5 | 6.5 | 0 | −3.5 | −0.6 | 50 |
| 342 | 1.5 | 6.5 | 0 | −3.5 | −0.5 | 50 |
| 343 | 1.5 | 6.5 | 0 | −3.2 | −0.4 | 50 |
| 344 | 1.5 | 6.5 | 0 | −3.4 | −0.4 | 50 |
| 345 | 1.5 | 6.5 | 0 | −3.1 | −0.3 | 50 |
| 346 | 1.5 | 6.5 | 0 | −3.3 | −0.3 | 50 |
| 347 | 1.5 | 6.5 | 0 | −3.3 | −0.3 | 50 |
| 348 | 1.5 | 6.5 | 0 | −3.6 | −0.3 | 50 |
| 349 | 1.5 | 6.5 | 0 | −3.6 | −0.2 | 50 |
| 350 | 1.5 | 6.5 | 0 | −3.7 | −0.2 | 50 |
| 351 | 2 | 6.5 | 0 | 0.2 | −0.1 | 50 |
| 352 | 2 | 6.5 | 0 | 0.5 | 2.1 | 50 |
| 353 | 2 | 6.5 | 0 | −0.2 | −2.4 | 50 |
| 354 | 2 | 6.5 | 0 | −2.6 | 0.7 | 50 |
| 355 | 2 | 6.5 | 0 | −2.5 | 1 | 50 |
| 356 | 2 | 6.5 | 0 | −2.4 | 1.1 | 50 |
| 357 | 2 | 6.5 | 0 | 0.4 | 2.4 | 50 |
| 358 | 2 | 6.5 | 0 | 2.6 | −0.4 | 50 |
| 359 | 2 | 6.5 | 0 | 2.1 | −1.6 | 50 |
| 360 | 2 | 6.5 | 0 | −2.9 | 0.2 | 50 |
| 361 | 2 | 6.5 | 0 | −2.7 | 0.5 | 50 |
| 362 | 2 | 6.5 | 0 | −2.8 | 0.6 | 50 |
| 363 | 2 | 6.5 | 0 | −2.7 | 0.8 | 50 |
| 364 | 2 | 6.5 | 0 | −2.8 | 1.1 | 50 |
| 365 | 2 | 6.5 | 0 | −2.8 | 1.1 | 50 |
| 366 | 2 | 6.5 | 0 | −2.6 | 1.5 | 50 |
| 367 | 2 | 6.5 | 0 | −2.6 | 1.5 | 50 |
| 368 | 2 | 6.5 | 0 | −2.4 | 1.6 | 50 |
| 369 | 2 | 6.5 | 0 | −2.3 | 1.7 | 50 |
| 370 | 2 | 6.5 | 0 | −2.3 | 1.7 | 50 |
| 371 | 2 | 6.5 | 0 | −2.3 | 1.8 | 50 |
| 372 | 2 | 6.5 | 0 | −2.3 | 1.8 | 50 |
| 373 | 2 | 6.5 | 0 | −2 | 2.1 | 50 |
| 374 | 2 | 6.5 | 0 | −1.8 | 2.1 | 50 |
| 375 | 2 | 6.5 | 0 | −1.9 | 2.3 | 50 |
| 376 | 2 | 6.5 | 0 | −1.8 | 2.2 | 50 |
| 377 | 2 | 6.5 | 0 | −1.8 | 2.4 | 50 |
| 378 | 2 | 6.5 | 0 | −1.5 | 2.4 | 50 |
| 379 | 2 | 6.5 | 0 | −1.5 | 2.5 | 50 |
| 380 | 2 | 6.5 | 0 | −1.4 | 2.6 | 50 |
| 381 | 2 | 6.5 | 0 | −1.3 | 2.5 | 50 |
| 382 | 2 | 6.5 | 0 | 2 | 2.1 | 50 |
| 383 | 2 | 6.5 | 0 | 2.9 | 0.1 | 50 |
| 384 | 2 | 6.5 | 0 | 3 | 0.1 | 50 |
| 385 | 2 | 6.5 | 0 | 2.8 | −0.2 | 50 |
| 386 | 2 | 6.5 | 0 | 2.9 | −0.4 | 50 |
| 387 | 2 | 6.5 | 0 | 2.8 | −0.6 | 50 |
| 388 | 2 | 6.5 | 0 | 2.9 | −0.7 | 50 |
| 389 | 2 | 6.5 | 0 | 2.7 | −0.7 | 50 |
| 390 | 2 | 6.5 | 0 | 2.9 | −0.8 | 50 |
| 391 | 2 | 6.5 | 0 | 2.7 | −1.1 | 50 |
| 392 | 2 | 6.5 | 0 | 2.4 | −1.7 | 50 |
| 393 | 2 | 6.5 | 0 | 2.1 | −1.9 | 50 |
| 394 | 2 | 6.5 | 0 | 2.2 | −2 | 50 |
| 395 | 2 | 6.5 | 0 | 2 | −1.9 | 50 |
| 396 | 2 | 6.5 | 0 | 1.8 | −2.1 | 50 |
| 397 | 2 | 6.5 | 0 | 1.8 | −2.3 | 50 |
| 398 | 2 | 6.5 | 0 | 1.8 | −2.4 | 50 |
| 399 | 2 | 6.5 | 0 | 1.6 | −2.4 | 50 |
| 400 | 2 | 6.5 | 0 | 1.5 | −2.4 | 50 |
| 401 | 2 | 6.5 | 0 | 1.4 | −2.6 | 50 |
| 402 | 2 | 6.5 | 0 | 1.2 | −2.7 | 50 |
| 403 | 2 | 6.5 | 0 | 0.8 | −2.9 | 50 |
| 404 | 2 | 6.5 | 0 | 0.5 | −2.7 | 50 |
| 405 | 2 | 6.5 | 0 | −2.9 | −0.4 | 50 |
| 406 | 2 | 6.5 | 0 | −2.9 | −0.2 | 50 |
| 407 | 2 | 6.5 | 0 | −3.1 | 0.1 | 50 |
| 408 | 2 | 6.5 | 0 | −3.2 | 0.2 | 50 |
| 409 | 2 | 6.5 | 0 | −3.1 | 0.5 | 50 |
| 410 | 2 | 6.5 | 0 | −3.2 | 0.8 | 50 |
| 411 | 2 | 6.5 | 0 | −3.1 | 0.9 | 50 |
| 412 | 2 | 6.5 | 0 | −2.9 | 1 | 50 |
| 413 | 2 | 6.5 | 0 | −3 | 1.1 | 50 |
| 414 | 2 | 6.5 | 0 | −2.8 | 1.3 | 50 |
| 415 | 2 | 6.5 | 0 | −2.7 | 1.4 | 50 |
| 416 | 2 | 6.5 | 0 | −3.2 | 1.7 | 50 |
| 417 | 2 | 6.5 | 0 | −2.9 | 1.7 | 50 |
| 418 | 2 | 6.5 | 0 | −3 | 1.8 | 50 |
| 419 | 2 | 6.5 | 0 | −2.7 | 1.8 | 50 |
| 420 | 2 | 6.5 | 0 | −2.6 | 1.9 | 50 |
| 421 | 2 | 6.5 | 0 | −2.5 | 1.9 | 50 |
| 422 | 2 | 6.5 | 0 | −2.7 | 2.3 | 50 |
| 423 | 2 | 6.5 | 0 | −2.7 | 2.4 | 50 |
| 424 | 2 | 6.5 | 0 | −2.3 | 2.1 | 50 |
| 425 | 2 | 6.5 | 0 | −2.2 | 2.1 | 50 |

APPENDIX I-continued

| | | | | | | |
|---|---|---|---|---|---|---|
| 426 | 2 | 6.5 | 0 | −2.5 | 2.7 | 50 |
| 427 | 2 | 6.5 | 0 | −2.1 | 2.4 | 50 |
| 428 | 2 | 6.5 | 0 | −2.4 | 2.8 | 50 |
| 429 | 2 | 6.5 | 0 | −2.1 | 2.6 | 50 |
| 430 | 2 | 6.5 | 0 | −2.1 | 2.7 | 50 |
| 431 | 2 | 6.5 | 0 | −2.1 | 2.7 | 50 |
| 432 | 2 | 6.5 | 0 | −2.2 | 2.9 | 50 |
| 433 | 2 | 6.5 | 0 | −1.7 | 2.6 | 50 |
| 434 | 2 | 6.5 | 0 | −1.8 | 3 | 50 |
| 435 | 2 | 6.5 | 0 | −1.6 | 2.8 | 50 |
| 436 | 2 | 6.5 | 0 | −1.5 | 2.9 | 50 |
| 437 | 2 | 6.5 | 0 | −1.3 | 3.1 | 50 |
| 438 | 2 | 6.5 | 0 | −1.5 | 3.6 | 50 |
| 439 | 2 | 6.5 | 0 | −1.1 | 3.3 | 50 |
| 440 | 2 | 6.5 | 0 | −0.9 | 3.2 | 50 |
| 441 | 2 | 6.5 | 0 | −0.9 | 3.3 | 50 |
| 442 | 2 | 6.5 | 0 | −0.8 | 3 | 50 |
| 443 | 2 | 6.5 | 0 | −0.9 | 3.6 | 50 |
| 444 | 2 | 6.5 | 0 | −0.7 | 3.5 | 50 |
| 445 | 2 | 6.5 | 0 | −0.5 | 3.3 | 50 |
| 446 | 2 | 6.5 | 0 | −0.5 | 3.3 | 50 |
| 447 | 2 | 6.5 | 0 | −0.4 | 3.4 | 50 |
| 448 | 2 | 6.5 | 0 | −0.4 | 3.5 | 50 |
| 449 | 2 | 6.5 | 0 | −0.3 | 3.7 | 50 |
| 450 | 2 | 6.5 | 0 | 0.1 | 3.6 | 50 |
| 451 | 2 | 6.5 | 0 | 0.2 | 3.2 | 50 |
| 452 | 2 | 6.5 | 0 | 0.2 | 3.2 | 50 |
| 453 | 2 | 6.5 | 0 | 0.3 | 3.6 | 50 |
| 454 | 2 | 6.5 | 0 | 0.3 | 3.4 | 50 |
| 455 | 2 | 6.5 | 0 | 0.3 | 3 | 50 |
| 456 | 2 | 6.5 | 0 | 0.5 | 3.5 | 50 |
| 457 | 2 | 6.5 | 0 | 0.9 | 3.7 | 50 |
| 458 | 2 | 6.5 | 0 | 1.2 | 3.6 | 50 |
| 459 | 2 | 6.5 | 0 | 1.1 | 3.1 | 50 |
| 460 | 2 | 6.5 | 0 | 3.2 | 1.3 | 50 |
| 461 | 2 | 6.5 | 0 | 3.3 | 1 | 50 |
| 462 | 2 | 6.5 | 0 | 3.3 | 0.8 | 50 |
| 463 | 2 | 6.5 | 0 | 3.2 | 0.3 | 50 |
| 464 | 2 | 6.5 | 0 | 3.3 | 0.1 | 50 |
| 465 | 2 | 6.5 | 0 | 3.1 | 0 | 50 |
| 466 | 2 | 6.5 | 0 | 3.1 | −0.1 | 50 |
| 467 | 2 | 6.5 | 0 | 3.1 | −0.4 | 50 |
| 468 | 2 | 6.5 | 0 | 3.3 | −0.5 | 50 |
| 469 | 2 | 6.5 | 0 | 3.2 | −0.5 | 50 |
| 470 | 2 | 6.5 | 0 | 3.2 | −0.6 | 50 |
| 471 | 2 | 6.5 | 0 | 3.4 | −0.8 | 50 |
| 472 | 2 | 6.5 | 0 | 3.1 | −0.8 | 50 |
| 473 | 2 | 6.5 | 0 | 3 | −0.8 | 50 |
| 474 | 2 | 6.5 | 0 | 3.2 | −1 | 50 |
| 475 | 2 | 6.5 | 0 | 3.1 | −1 | 50 |
| 476 | 2 | 6.5 | 0 | 3.2 | −1.3 | 50 |
| 477 | 2 | 6.5 | 0 | 3.1 | −1.3 | 50 |
| 478 | 2 | 6.5 | 0 | 3 | −1.3 | 50 |
| 479 | 2 | 6.5 | 0 | 2.8 | −1.3 | 50 |
| 480 | 2 | 6.5 | 0 | 3.1 | −1.8 | 50 |
| 481 | 2 | 6.5 | 0 | 2.7 | −1.9 | 50 |
| 482 | 2 | 6.5 | 0 | 2.6 | −1.9 | 50 |
| 483 | 2 | 6.5 | 0 | 2.4 | −2 | 50 |
| 484 | 2 | 6.5 | 0 | 2.8 | −2.5 | 50 |
| 485 | 2 | 6.5 | 0 | 2.2 | −2.1 | 50 |
| 486 | 2 | 6.5 | 0 | 2.6 | −2.5 | 50 |
| 487 | 2 | 6.5 | 0 | 2.4 | −2.4 | 50 |
| 488 | 2 | 6.5 | 0 | 2.2 | −2.4 | 50 |
| 489 | 2 | 6.5 | 0 | 2.2 | −2.4 | 50 |
| 490 | 2 | 6.5 | 0 | 2.3 | −2.8 | 50 |
| 491 | 2 | 6.5 | 0 | 2.2 | −2.7 | 50 |
| 492 | 2 | 6.5 | 0 | 1.9 | −2.8 | 50 |
| 493 | 2 | 6.5 | 0 | 1.9 | −2.9 | 50 |
| 494 | 2 | 6.5 | 0 | 1.9 | −3.1 | 50 |
| 495 | 2 | 6.5 | 0 | 1.8 | −3.1 | 50 |
| 496 | 2 | 6.5 | 0 | 1.8 | −3.2 | 50 |
| 497 | 2 | 6.5 | 0 | 1.4 | −2.7 | 50 |
| 498 | 2 | 6.5 | 0 | 1.6 | −3.3 | 50 |
| 499 | 2 | 6.5 | 0 | 1.6 | −3.3 | 50 |
| 500 | 2 | 6.5 | 0 | 1.6 | −3.4 | 50 |
| 501 | 2 | 6.5 | 0 | 1.4 | −3.1 | 50 |
| 502 | 2 | 6.5 | 0 | 1.4 | −3.2 | 50 |
| 503 | 2 | 6.5 | 0 | 1.3 | −3.4 | 50 |
| 504 | 2 | 6.5 | 0 | 1.1 | −2.9 | 50 |
| 505 | 2 | 6.5 | 0 | 1.2 | −3.2 | 50 |
| 506 | 2 | 6.5 | 0 | 1.2 | −3.3 | 50 |
| 507 | 2 | 6.5 | 0 | 1.2 | −3.5 | 50 |
| 508 | 2 | 6.5 | 0 | 1.1 | −3.4 | 50 |
| 509 | 2 | 6.5 | 0 | 0.9 | −2.9 | 50 |
| 510 | 2 | 6.5 | 0 | 0.9 | −2.9 | 50 |
| 511 | 2 | 6.5 | 0 | 0.9 | −2.9 | 50 |
| 512 | 2 | 6.5 | 0 | 1.1 | −3.6 | 50 |
| 513 | 2 | 6.5 | 0 | 1 | −3.4 | 50 |
| 514 | 2 | 6.5 | 0 | 0.8 | −3.2 | 50 |
| 515 | 2 | 6.5 | 0 | 0.7 | −3.7 | 50 |
| 516 | 2 | 6.5 | 0 | 0.5 | −3.6 | 50 |
| 517 | 2 | 6.5 | 0 | 0.4 | −3.6 | 50 |
| 518 | 2 | 6.5 | 0 | 0.3 | −3.7 | 50 |
| 519 | 2 | 6.5 | 0 | 0.2 | −3.2 | 50 |
| 520 | 2 | 6.5 | 0 | 0.1 | −3.1 | 50 |
| 521 | 2 | 6.5 | 0 | −0.1 | −3.7 | 50 |
| 522 | 2 | 6.5 | 0 | −0.2 | −3.7 | 50 |
| 523 | 2 | 6.5 | 0 | −0.3 | −3.7 | 50 |
| 524 | 2 | 6.5 | 0 | −0.3 | −3.6 | 50 |
| 525 | 2 | 6.5 | 0 | −0.4 | −3.7 | 50 |
| 526 | 2 | 6.5 | 0 | −0.6 | −3.7 | 50 |
| 527 | 2 | 6.5 | 0 | −0.7 | −3.7 | 50 |
| 528 | 2 | 6.5 | 0 | −0.6 | −3.1 | 50 |
| 529 | 2 | 6.5 | 0 | −1 | −3.6 | 50 |
| 530 | 2 | 6.5 | 0 | −1.1 | −2.9 | 50 |
| 531 | 2 | 6.5 | 0 | −1.8 | −2.5 | 50 |
| 532 | 2 | 6.5 | 0 | −2.9 | −1.7 | 50 |
| 533 | 2 | 6.5 | 0 | −3.1 | −1.4 | 50 |
| 534 | 2 | 6.5 | 0 | −3 | −1.3 | 50 |
| 535 | 2 | 6.5 | 0 | −3.2 | −0.9 | 50 |
| 536 | 2 | 6.5 | 0 | −3 | −0.5 | 50 |
| 537 | 2 | 6.5 | 0 | −3.2 | −0.3 | 50 |
| 538 | 2.5 | 6.5 | 0 | 1.3 | 1.3 | 50 |
| 539 | 2.5 | 6.5 | 0 | −2.2 | 0.7 | 50 |
| 540 | 2.5 | 6.5 | 0 | 1.4 | 1.9 | 50 |
| 541 | 2.5 | 6.5 | 0 | −2.3 | −0.7 | 50 |
| 542 | 2.5 | 6.5 | 0 | −2.6 | 0.4 | 50 |
| 543 | 2.5 | 6.5 | 0 | −1.5 | 2 | 50 |
| 544 | 2.5 | 6.5 | 0 | −0.8 | 2.3 | 50 |
| 545 | 2.5 | 6.5 | 0 | 2.5 | 1 | 50 |
| 546 | 2.5 | 6.5 | 0 | 2.5 | 0.1 | 50 |
| 547 | 2.5 | 6.5 | 0 | 2.7 | −0.2 | 50 |
| 548 | 2.5 | 6.5 | 0 | 2.5 | −0.5 | 50 |
| 549 | 2.5 | 6.5 | 0 | 2.4 | −1.1 | 50 |
| 550 | 2.5 | 6.5 | 0 | 1.7 | −2 | 50 |
| 551 | 2.5 | 6.5 | 0 | 1.4 | −2 | 50 |
| 552 | 2.5 | 6.5 | 0 | 1.3 | −2.1 | 50 |
| 553 | 2.5 | 6.5 | 0 | 0.9 | −2.5 | 50 |
| 554 | 2.5 | 6.5 | 0 | 0.5 | −2.6 | 50 |
| 555 | 2.5 | 6.5 | 0 | −0.2 | −2.6 | 50 |
| 556 | 2.5 | 6.5 | 0 | −1.6 | −2.1 | 50 |
| 557 | 2.5 | 6.5 | 0 | −2.6 | 0 | 50 |
| 558 | 2.5 | 6.5 | 0 | −2.9 | 0.1 | 50 |
| 559 | 2.5 | 6.5 | 0 | −2.9 | 0.1 | 50 |
| 560 | 2.5 | 6.5 | 0 | −2.9 | 0.3 | 50 |
| 561 | 2.5 | 6.5 | 0 | −2.5 | 1.6 | 50 |
| 562 | 2.5 | 6.5 | 0 | −2.2 | 1.6 | 50 |
| 563 | 2.5 | 6.5 | 0 | −2.2 | 1.8 | 50 |
| 564 | 2.5 | 6.5 | 0 | −2.3 | 1.9 | 50 |
| 565 | 2.5 | 6.5 | 0 | −2.3 | 1.9 | 50 |
| 566 | 2.5 | 6.5 | 0 | −1.9 | 2.3 | 50 |
| 567 | 2.5 | 6.5 | 0 | −1.7 | 2.2 | 50 |
| 568 | 2.5 | 6.5 | 0 | −1.5 | 2.6 | 50 |
| 569 | 2.5 | 6.5 | 0 | −1.3 | 2.6 | 50 |
| 570 | 2.5 | 6.5 | 0 | −0.8 | 2.6 | 50 |
| 571 | 2.5 | 6.5 | 0 | −0.6 | 2.7 | 50 |
| 572 | 2.5 | 6.5 | 0 | 1.7 | 2.3 | 50 |
| 573 | 2.5 | 6.5 | 0 | 2.7 | 1.2 | 50 |
| 574 | 2.5 | 6.5 | 0 | 2.8 | 1.1 | 50 |
| 575 | 2.5 | 6.5 | 0 | 2.8 | 0.5 | 50 |
| 576 | 2.5 | 6.5 | 0 | 2.8 | 0.3 | 50 |
| 577 | 2.5 | 6.5 | 0 | 2.9 | 0 | 50 |
| 578 | 2.5 | 6.5 | 0 | 2.6 | −1 | 50 |
| 579 | 2.5 | 6.5 | 0 | 2.6 | −1.5 | 50 |
| 580 | 2.5 | 6.5 | 0 | 2.4 | −1.8 | 50 |
| 581 | 2.5 | 6.5 | 0 | 2.2 | −1.7 | 50 |
| 582 | 2.5 | 6.5 | 0 | 2.2 | −2 | 50 |
| 583 | 2.5 | 6.5 | 0 | 2 | −2.2 | 50 |

APPENDIX I-continued

| | | | | | | |
|---|---|---|---|---|---|---|
| 584 | 2.5 | 6.5 | 0 | 1.7 | −2.4 | 50 |
| 585 | 2.5 | 6.5 | 0 | 1.6 | −2.5 | 50 |
| 586 | 2.5 | 6.5 | 0 | 1.6 | −2.5 | 50 |
| 587 | 2.5 | 6.5 | 0 | 1 | −2.6 | 50 |
| 588 | 2.5 | 6.5 | 0 | 0.3 | −2.7 | 50 |
| 589 | 2.5 | 6.5 | 0 | −1.2 | −2.7 | 50 |
| 590 | 2.5 | 6.5 | 0 | −2.8 | −0.6 | 50 |
| 591 | 2.5 | 6.5 | 0 | −3 | 0.3 | 50 |
| 592 | 2.5 | 6.5 | 0 | −3.1 | 0.5 | 50 |
| 593 | 2.5 | 6.5 | 0 | −3.1 | 1 | 50 |
| 594 | 2.5 | 6.5 | 0 | −2.9 | 1.2 | 50 |
| 595 | 2.5 | 6.5 | 0 | −2.7 | 1.4 | 50 |
| 596 | 2.5 | 6.5 | 0 | −2.6 | 1.8 | 50 |
| 597 | 2.5 | 6.5 | 0 | −2.4 | 2 | 50 |
| 598 | 2.5 | 6.5 | 0 | −2.4 | 2.1 | 50 |
| 599 | 2.5 | 6.5 | 0 | −2.4 | 2.4 | 50 |
| 600 | 2.5 | 6.5 | 0 | −2.4 | 2.5 | 50 |
| 601 | 2.5 | 6.5 | 0 | −2.2 | 2.3 | 50 |
| 602 | 2.5 | 6.5 | 0 | −2.2 | 2.6 | 50 |
| 603 | 2.5 | 6.5 | 0 | −2 | 2.6 | 50 |
| 604 | 2.5 | 6.5 | 0 | −2.1 | 2.8 | 50 |
| 605 | 2.5 | 6.5 | 0 | −1.7 | 2.5 | 50 |
| 606 | 2.5 | 6.5 | 0 | −1.7 | 2.8 | 50 |
| 607 | 2.5 | 6.5 | 0 | −1.5 | 2.7 | 50 |
| 608 | 2.5 | 6.5 | 0 | −1.6 | 3.1 | 50 |
| 609 | 2.5 | 6.5 | 0 | −1.4 | 3 | 50 |
| 610 | 2.5 | 6.5 | 0 | −1.3 | 3 | 50 |
| 611 | 2.5 | 6.5 | 0 | −1.4 | 3.3 | 50 |
| 612 | 2.5 | 6.5 | 0 | −1.1 | 3 | 50 |
| 613 | 2.5 | 6.5 | 0 | −1.1 | 3.3 | 50 |
| 614 | 2.5 | 6.5 | 0 | −1 | 3.4 | 50 |
| 615 | 2.5 | 6.5 | 0 | −0.9 | 3.2 | 50 |
| 616 | 2.5 | 6.5 | 0 | −0.7 | 3.4 | 50 |
| 617 | 2.5 | 6.5 | 0 | −0.5 | 3.1 | 50 |
| 618 | 2.5 | 6.5 | 0 | −0.3 | 3.4 | 50 |
| 619 | 2.5 | 6.5 | 0 | −0.2 | 3.3 | 50 |
| 620 | 2.5 | 6.5 | 0 | −0.1 | 3.1 | 50 |
| 621 | 2.5 | 6.5 | 0 | 0 | 3.4 | 50 |
| 622 | 2.5 | 6.5 | 0 | 0.7 | 3.1 | 50 |
| 623 | 2.5 | 6.5 | 0 | 1.2 | 2.8 | 50 |
| 624 | 2.5 | 6.5 | 0 | 1.4 | 3.2 | 50 |
| 625 | 2.5 | 6.5 | 0 | 2.9 | 1.6 | 50 |
| 626 | 2.5 | 6.5 | 0 | 3 | 1.2 | 50 |
| 627 | 2.5 | 6.5 | 0 | 3 | 0.4 | 50 |
| 628 | 2.5 | 6.5 | 0 | 3 | −0.5 | 50 |
| 629 | 2.5 | 6.5 | 0 | 3 | −0.6 | 50 |
| 630 | 2.5 | 6.5 | 0 | 3 | −0.8 | 50 |
| 631 | 2.5 | 6.5 | 0 | 3 | −0.9 | 50 |
| 632 | 2.5 | 6.5 | 0 | 2.9 | −1.2 | 50 |
| 633 | 2.5 | 6.5 | 0 | 2.8 | −1.7 | 50 |
| 634 | 2.5 | 6.5 | 0 | 2.9 | −1.8 | 50 |
| 635 | 2.5 | 6.5 | 0 | 2.6 | −1.7 | 50 |
| 636 | 2.5 | 6.5 | 0 | 2.8 | −1.9 | 50 |
| 637 | 2.5 | 6.5 | 0 | 2.6 | −1.8 | 50 |
| 638 | 2.5 | 6.5 | 0 | 2.6 | −1.8 | 50 |
| 639 | 2.5 | 6.5 | 0 | 2.4 | −2 | 50 |
| 640 | 2.5 | 6.5 | 0 | 2.2 | −2.1 | 50 |
| 641 | 2.5 | 6.5 | 0 | 2.4 | −2.3 | 50 |
| 642 | 2.5 | 6.5 | 0 | 2.1 | −2.2 | 50 |
| 643 | 2.5 | 6.5 | 0 | 2.1 | −2.5 | 50 |
| 644 | 2.5 | 6.5 | 0 | 2 | −2.5 | 50 |
| 645 | 2.5 | 6.5 | 0 | 1.9 | −2.4 | 50 |
| 646 | 2.5 | 6.5 | 0 | 2.1 | −2.7 | 50 |
| 647 | 2.5 | 6.5 | 0 | 1.8 | −2.7 | 50 |
| 648 | 2.5 | 6.5 | 0 | 1.7 | −2.9 | 50 |
| 649 | 2.5 | 6.5 | 0 | 1.7 | −3.2 | 50 |
| 650 | 2.5 | 6.5 | 0 | 1.5 | −3 | 50 |
| 651 | 2.5 | 6.5 | 0 | 1.1 | −3.1 | 50 |
| 652 | 2.5 | 6.5 | 0 | 1.1 | −3.3 | 50 |
| 653 | 2.5 | 6.5 | 0 | 0.9 | −3 | 50 |
| 654 | 2.5 | 6.5 | 0 | 0.6 | −3.4 | 50 |
| 655 | 2.5 | 6.5 | 0 | 0.5 | −3.3 | 50 |
| 656 | 2.5 | 6.5 | 0 | 0.4 | −3.4 | 50 |
| 657 | 2.5 | 6.5 | 0 | 0.2 | −3.4 | 50 |
| 658 | 2.5 | 6.5 | 0 | 0 | −3.4 | 50 |
| 659 | 2.5 | 6.5 | 0 | −0.3 | −3.4 | 50 |
| 660 | 2.5 | 6.5 | 0 | −0.4 | −3.4 | 50 |
| 661 | 2.5 | 6.5 | 0 | −0.6 | −3.4 | 50 |
| 662 | 2.5 | 6.5 | 0 | −0.7 | −3.4 | 50 |
| 663 | 2.5 | 6.5 | 0 | −0.8 | −3.3 | 50 |
| 664 | 2.5 | 6.5 | 0 | −0.9 | −3.1 | 50 |
| 665 | 2.5 | 6.5 | 0 | −3.1 | −0.9 | 50 |
| 666 | 2.5 | 6.5 | 0 | −3 | −0.6 | 50 |
| 667 | 2.5 | 6.5 | 0 | −3.1 | −0.2 | 50 |
| 668 | 3 | 6.5 | 0 | −2.4 | 0.2 | 50 |
| 669 | 3 | 6.5 | 0 | −2.2 | 0.4 | 50 |
| 670 | 3 | 6.5 | 0 | −1.8 | 1.4 | 50 |
| 671 | 3 | 6.5 | 0 | 2.3 | −0.5 | 50 |
| 672 | 3 | 6.5 | 0 | 1.7 | −1.7 | 50 |
| 673 | 3 | 6.5 | 0 | 1.5 | −1.6 | 50 |
| 674 | 3 | 6.5 | 0 | 1.6 | −1.8 | 50 |
| 675 | 3 | 6.5 | 0 | −0.6 | −2.2 | 50 |
| 676 | 3 | 6.5 | 0 | −2 | −0.7 | 50 |
| 677 | 3 | 6.5 | 0 | −2.6 | 0.7 | 50 |
| 678 | 3 | 6.5 | 0 | −2.3 | 1.3 | 50 |
| 679 | 3 | 6.5 | 0 | −2.1 | 1.3 | 50 |
| 680 | 3 | 6.5 | 0 | −1.9 | 1.5 | 50 |
| 681 | 3 | 6.5 | 0 | −1.6 | 2 | 50 |
| 682 | 3 | 6.5 | 0 | −1.2 | 2.3 | 50 |
| 683 | 3 | 6.5 | 0 | −1.2 | 2.3 | 50 |
| 684 | 3 | 6.5 | 0 | −1.2 | 2.4 | 50 |
| 685 | 3 | 6.5 | 0 | −0.6 | 2.6 | 50 |
| 686 | 3 | 6.5 | 0 | 2.4 | 1 | 50 |
| 687 | 3 | 6.5 | 0 | 2.5 | 0.4 | 50 |
| 688 | 3 | 6.5 | 0 | 2.3 | −1.1 | 50 |
| 689 | 3 | 6.5 | 0 | 2.2 | −1.3 | 50 |
| 690 | 3 | 6.5 | 0 | 2.1 | −1.6 | 50 |
| 691 | 3 | 6.5 | 0 | 1.9 | −1.8 | 50 |
| 692 | 3 | 6.5 | 0 | −0.7 | −2.5 | 50 |
| 693 | 3 | 6.5 | 0 | −2.9 | 0.4 | 50 |
| 694 | 3 | 6.5 | 0 | −2.7 | 0.4 | 50 |
| 695 | 3 | 6.5 | 0 | −2.8 | 0.5 | 50 |
| 696 | 3 | 6.5 | 0 | −2.8 | 0.5 | 50 |
| 697 | 3 | 6.5 | 0 | −2.8 | 0.7 | 50 |
| 698 | 3 | 6.5 | 0 | −2.7 | 0.9 | 50 |
| 699 | 3 | 6.5 | 0 | −2.8 | 1.1 | 50 |
| 700 | 3 | 6.5 | 0 | −2.8 | 1.1 | 50 |
| 701 | 3 | 6.5 | 0 | −2.6 | 1.3 | 50 |
| 702 | 3 | 6.5 | 0 | −2.4 | 1.3 | 50 |
| 703 | 3 | 6.5 | 0 | −2.4 | 1.8 | 50 |
| 704 | 3 | 6.5 | 0 | −2.2 | 1.9 | 50 |
| 705 | 3 | 6.5 | 0 | −2 | 2.2 | 50 |
| 706 | 3 | 6.5 | 0 | −1.6 | 2.2 | 50 |
| 707 | 3 | 6.5 | 0 | −1.7 | 2.4 | 50 |
| 708 | 3 | 6.5 | 0 | −1.3 | 2.5 | 50 |
| 709 | 3 | 6.5 | 0 | −1.3 | 2.7 | 50 |
| 710 | 3 | 6.5 | 0 | −1.2 | 2.5 | 50 |
| 711 | 3 | 6.5 | 0 | −0.9 | 2.7 | 50 |
| 712 | 3 | 6.5 | 0 | 0.1 | 2.9 | 50 |
| 713 | 3 | 6.5 | 0 | 0.3 | 2.8 | 50 |
| 714 | 3 | 6.5 | 0 | 0.7 | 2.9 | 50 |
| 715 | 3 | 6.5 | 0 | 2.7 | −0.3 | 50 |
| 716 | 3 | 6.5 | 0 | 2.7 | −0.3 | 50 |
| 717 | 3 | 6.5 | 0 | 2.7 | −0.4 | 50 |
| 718 | 3 | 6.5 | 0 | 2.8 | −0.8 | 50 |
| 719 | 3 | 6.5 | 0 | 2.5 | −1.2 | 50 |
| 720 | 3 | 6.5 | 0 | 2.6 | −1.5 | 50 |
| 721 | 3 | 6.5 | 0 | 2.3 | −1.8 | 50 |
| 722 | 3 | 6.5 | 0 | 2.3 | −1.9 | 50 |
| 723 | 3 | 6.5 | 0 | 2.1 | −1.9 | 50 |
| 724 | 3 | 6.5 | 0 | 1.8 | −2.4 | 50 |
| 725 | 3 | 6.5 | 0 | 1.8 | −2.4 | 50 |
| 726 | 3 | 6.5 | 0 | 1.5 | −2.4 | 50 |
| 727 | 3 | 6.5 | 0 | 1.5 | −2.6 | 50 |
| 728 | 3 | 6.5 | 0 | 1.4 | −2.6 | 50 |
| 729 | 3 | 6.5 | 0 | 1.3 | −2.5 | 50 |
| 730 | 3 | 6.5 | 0 | 1 | −2.6 | 50 |
| 731 | 3 | 6.5 | 0 | 0.8 | −2.8 | 50 |
| 732 | 3 | 6.5 | 0 | 0.3 | −2.7 | 50 |
| 733 | 3 | 6.5 | 0 | 0 | −3 | 50 |
| 734 | 3 | 6.5 | 0 | −2.6 | −0.8 | 50 |
| 735 | 3 | 6.5 | 0 | −2.7 | −0.5 | 50 |
| 736 | 3 | 6.5 | 0 | −2.6 | 1.8 | 50 |
| 737 | 3 | 6.5 | 0 | −2.4 | 1.9 | 50 |
| 738 | 3 | 6.5 | 0 | −2.2 | 2.1 | 50 |
| 739 | 3 | 6.5 | 0 | −2 | 2.4 | 50 |
| 740 | 3 | 6.5 | 0 | −1.6 | 2.6 | 50 |
| 741 | 3 | 6.5 | 0 | −1.5 | 2.9 | 50 |

APPENDIX I-continued

| | | | | | | |
|---|---|---|---|---|---|---|
| 742 | 3 | 6.5 | 0 | −1.5 | 3 | 50 |
| 743 | 3 | 6.5 | 0 | −1 | 3.2 | 50 |
| 744 | 3 | 6.5 | 0 | −0.9 | 3 | 50 |
| 745 | 3 | 6.5 | 0 | −0.9 | 3.2 | 50 |
| 746 | 3 | 6.5 | 0 | −0.9 | 3.2 | 50 |
| 747 | 3 | 6.5 | 0 | −0.8 | 3.1 | 50 |
| 748 | 3 | 6.5 | 0 | −0.7 | 3 | 50 |
| 749 | 3 | 6.5 | 0 | −0.4 | 3 | 50 |
| 750 | 3 | 6.5 | 0 | −0.4 | 3.1 | 50 |
| 751 | 3 | 6.5 | 0 | −0.2 | 3.2 | 50 |
| 752 | 3 | 6.5 | 0 | 0 | 3.1 | 50 |
| 753 | 3 | 6.5 | 0 | 1.9 | 2.5 | 50 |
| 754 | 3 | 6.5 | 0 | 2.5 | −1.8 | 50 |
| 755 | 3 | 6.5 | 0 | 2.2 | −2.1 | 50 |
| 756 | 3 | 6.5 | 0 | 2.1 | −2.3 | 50 |
| 757 | 3 | 6.5 | 0 | 1.7 | −2.7 | 50 |
| 758 | 3 | 6.5 | 0 | 1.5 | −3 | 50 |
| 759 | 3 | 6.5 | 0 | 1.3 | −3.1 | 50 |
| 760 | 3 | 6.5 | 0 | 0.9 | −3.1 | 50 |
| 761 | 3 | 6.5 | 0 | 0.7 | −3.2 | 50 |
| 762 | 3 | 6.5 | 0 | 0.6 | −3.2 | 50 |
| 763 | 3 | 6.5 | 0 | 0.6 | −3.2 | 50 |
| 764 | 3 | 6.5 | 0 | 0.5 | −3.1 | 50 |
| 765 | 3 | 6.5 | 0 | 0.4 | −3.1 | 50 |
| 766 | 3 | 6.5 | 0 | 0.1 | −3.1 | 50 |
| 767 | 3 | 6.5 | 0 | −0.5 | −3.1 | 50 |
| 768 | 3 | 6.5 | 0 | −1 | −3 | 50 |
| 769 | 3.5 | 6.5 | 0 | −1.7 | 1 | 50 |
| 770 | 3.5 | 6.5 | 0 | −0.2 | 1.9 | 50 |
| 771 | 3.5 | 6.5 | 0 | 1.9 | 0.4 | 50 |
| 772 | 3.5 | 6.5 | 0 | 1.5 | −1.3 | 50 |
| 773 | 3.5 | 6.5 | 0 | 0.9 | −1.6 | 50 |
| 774 | 3.5 | 6.5 | 0 | −2.3 | 0.4 | 50 |
| 775 | 3.5 | 6.5 | 0 | −2.3 | 0.5 | 50 |
| 776 | 3.5 | 6.5 | 0 | −1.9 | 0.7 | 50 |
| 777 | 3.5 | 6.5 | 0 | −1.8 | 1.3 | 50 |
| 778 | 3.5 | 6.5 | 0 | −1.1 | 2.1 | 50 |
| 779 | 3.5 | 6.5 | 0 | −0.5 | 2.1 | 50 |
| 780 | 3.5 | 6.5 | 0 | −0.3 | 2.2 | 50 |
| 781 | 3.5 | 6.5 | 0 | 2.3 | 0.3 | 50 |
| 782 | 3.5 | 6.5 | 0 | 2.4 | 0.1 | 50 |
| 783 | 3.5 | 6.5 | 0 | 2.3 | −0.4 | 50 |
| 784 | 3.5 | 6.5 | 0 | 2.3 | −0.6 | 50 |
| 785 | 3.5 | 6.5 | 0 | 2.2 | −0.6 | 50 |
| 786 | 3.5 | 6.5 | 0 | 1.6 | −1.6 | 50 |
| 787 | 3.5 | 6.5 | 0 | 1.4 | −1.8 | 50 |
| 788 | 3.5 | 6.5 | 0 | 1.1 | −1.9 | 50 |
| 789 | 3.5 | 6.5 | 0 | 1 | −2 | 50 |
| 790 | 3.5 | 6.5 | 0 | −2.7 | 0.2 | 50 |
| 791 | 3.5 | 6.5 | 0 | −2.4 | 0.4 | 50 |
| 792 | 3.5 | 6.5 | 0 | −2.4 | 0.6 | 50 |
| 793 | 3.5 | 6.5 | 0 | −2.4 | 1 | 50 |
| 794 | 3.5 | 6.5 | 0 | −2.2 | 1.2 | 50 |
| 795 | 3.5 | 6.5 | 0 | −2.3 | 1.3 | 50 |
| 796 | 3.5 | 6.5 | 0 | −2.3 | 1.3 | 50 |
| 797 | 3.5 | 6.5 | 0 | −2.3 | 1.4 | 50 |
| 798 | 3.5 | 6.5 | 0 | −2 | 1.7 | 50 |
| 799 | 3.5 | 6.5 | 0 | −1.8 | 1.8 | 50 |
| 800 | 3.5 | 6.5 | 0 | −1.6 | 1.9 | 50 |
| 801 | 3.5 | 6.5 | 0 | −1.7 | 2.1 | 50 |
| 802 | 3.5 | 6.5 | 0 | −1.1 | 2.2 | 50 |
| 803 | 3.5 | 6.5 | 0 | 2.6 | 0.3 | 50 |
| 804 | 3.5 | 6.5 | 0 | 2.7 | −0.1 | 50 |
| 805 | 3.5 | 6.5 | 0 | 2.6 | −0.1 | 50 |
| 806 | 3.5 | 6.5 | 0 | 2.3 | −1.1 | 50 |
| 807 | 3.5 | 6.5 | 0 | 2.3 | −1.2 | 50 |
| 808 | 3.5 | 6.5 | 0 | 2.1 | −1.7 | 50 |
| 809 | 3.5 | 6.5 | 0 | 1.6 | −1.9 | 50 |
| 810 | 3.5 | 6.5 | 0 | 1.6 | −1.9 | 50 |
| 811 | 3.5 | 6.5 | 0 | −2.4 | −0.5 | 50 |
| 812 | 3.5 | 6.5 | 0 | −2.7 | −0.1 | 50 |
| 813 | 3.5 | 6.5 | 0 | −2.7 | −0.1 | 50 |
| 814 | 3.5 | 6.5 | 0 | −2.1 | 1.9 | 50 |
| 815 | 3.5 | 6.5 | 0 | −2.2 | 2 | 50 |
| 816 | 3.5 | 6.5 | 0 | −2 | 1.9 | 50 |
| 817 | 3.5 | 6.5 | 0 | −1.9 | 2.2 | 50 |
| 818 | 3.5 | 6.5 | 0 | −1.4 | 2.5 | 50 |
| 819 | 3.5 | 6.5 | 0 | −1.1 | 2.6 | 50 |
| 820 | 3.5 | 6.5 | 0 | −1.1 | 2.7 | 50 |
| 821 | 3.5 | 6.5 | 0 | −0.7 | 2.8 | 50 |
| 822 | 3.5 | 6.5 | 0 | 0.7 | 2.9 | 50 |
| 823 | 3.5 | 6.5 | 0 | 2.7 | −0.4 | 50 |
| 824 | 3.5 | 6.5 | 0 | 2.3 | −1.6 | 50 |
| 825 | 3.5 | 6.5 | 0 | 2.2 | −1.8 | 50 |
| 826 | 3.5 | 6.5 | 0 | 2.1 | −1.9 | 50 |
| 827 | 3.5 | 6.5 | 0 | 2 | −2.2 | 50 |
| 828 | 3.5 | 6.5 | 0 | 1.7 | −2.4 | 50 |
| 829 | 3.5 | 6.5 | 0 | 1.6 | −2.3 | 50 |
| 830 | 3.5 | 6.5 | 0 | 1.4 | −2.6 | 50 |
| 831 | 3.5 | 6.5 | 0 | 1 | −2.6 | 50 |
| 832 | 3.5 | 6.5 | 0 | −0.8 | −2.8 | 50 |
| 833 | 3.5 | 6.5 | 0 | −0.9 | 2.9 | 50 |
| 834 | 3.5 | 6.5 | 0 | 1.2 | −2.8 | 50 |
| 835 | 4 | 6.5 | 0 | −0.8 | −0.3 | 50 |
| 836 | 4 | 6.5 | 0 | 1.3 | −0.9 | 50 |
| 837 | 4 | 6.5 | 0 | 0.8 | −1.2 | 50 |
| 838 | 4 | 6.5 | 0 | −1.3 | −0.8 | 50 |
| 839 | 4 | 6.5 | 0 | −2 | 0.1 | 50 |
| 840 | 4 | 6.5 | 0 | −1.6 | 0.9 | 50 |
| 841 | 4 | 6.5 | 0 | −1.6 | 1.1 | 50 |
| 842 | 4 | 6.5 | 0 | −1.4 | 1 | 50 |
| 843 | 4 | 6.5 | 0 | −0.9 | 1.7 | 50 |
| 844 | 4 | 6.5 | 0 | −0.8 | 1.7 | 50 |
| 845 | 4 | 6.5 | 0 | −0.7 | 1.7 | 50 |
| 846 | 4 | 6.5 | 0 | −0.2 | 1.8 | 50 |
| 847 | 4 | 6.5 | 0 | 1.8 | −0.2 | 50 |
| 848 | 4 | 6.5 | 0 | 1.7 | −0.5 | 50 |
| 849 | 4 | 6.5 | 0 | 1.6 | −0.6 | 50 |
| 850 | 4 | 6.5 | 0 | 1.6 | −0.8 | 50 |
| 851 | 4 | 6.5 | 0 | 1.7 | −1 | 50 |
| 852 | 4 | 6.5 | 0 | 1.5 | −1 | 50 |
| 853 | 4 | 6.5 | 0 | 1.4 | −1.3 | 50 |
| 854 | 4 | 6.5 | 0 | 0.9 | −1.4 | 50 |
| 855 | 4 | 6.5 | 0 | −1.9 | 0 | 50 |
| 856 | 4 | 6.5 | 0 | −2.3 | 0.3 | 50 |
| 857 | 4 | 6.5 | 0 | −2.2 | 0.3 | 50 |
| 858 | 4 | 6.5 | 0 | −2 | 0.5 | 50 |
| 859 | 4 | 6.5 | 0 | −2 | 0.7 | 50 |
| 860 | 4 | 6.5 | 0 | −1.9 | 1 | 50 |
| 861 | 4 | 6.5 | 0 | −1.8 | 1.4 | 50 |
| 862 | 4 | 6.5 | 0 | −1.4 | 1.8 | 50 |
| 863 | 4 | 6.5 | 0 | −1.2 | 2 | 50 |
| 864 | 4 | 6.5 | 0 | −0.3 | 2.2 | 50 |
| 865 | 4 | 6.5 | 0 | 0.4 | 2.1 | 50 |
| 866 | 4 | 6.5 | 0 | 1.1 | 1.8 | 50 |
| 867 | 4 | 6.5 | 0 | 2.3 | 0.6 | 50 |
| 868 | 4 | 6.5 | 0 | 2.2 | −0.2 | 50 |
| 869 | 4 | 6.5 | 0 | 2.1 | −0.4 | 50 |
| 870 | 4 | 6.5 | 0 | 2.2 | −0.5 | 50 |
| 871 | 4 | 6.5 | 0 | 2 | −0.5 | 50 |
| 872 | 4 | 6.5 | 0 | 2.2 | −0.6 | 50 |
| 873 | 4 | 6.5 | 0 | 2.2 | −0.9 | 50 |
| 874 | 4 | 6.5 | 0 | 2.1 | −0.9 | 50 |
| 875 | 4 | 6.5 | 0 | 2.1 | −1 | 50 |
| 876 | 4 | 6.5 | 0 | 2 | −1.3 | 50 |
| 877 | 4 | 6.5 | 0 | 1.8 | −1.5 | 50 |
| 878 | 4 | 6.5 | 0 | 1.7 | −1.5 | 50 |
| 879 | 4 | 6.5 | 0 | 1.5 | −1.7 | 50 |
| 880 | 4 | 6.5 | 0 | 1.5 | −1.8 | 50 |
| 881 | 4 | 6.5 | 0 | 1.4 | −1.7 | 50 |
| 882 | 4 | 6.5 | 0 | 1.1 | −1.7 | 50 |
| 883 | 4 | 6.5 | 0 | 0.9 | −1.9 | 50 |
| 884 | 4 | 6.5 | 0 | 0.7 | −2.1 | 50 |
| 885 | 4 | 6.5 | 0 | 0.4 | −2.2 | 50 |
| 886 | 4 | 6.5 | 0 | −0.4 | −2.2 | 50 |
| 887 | 4 | 6.5 | 0 | −2.1 | −0.8 | 50 |
| 888 | 4 | 6.5 | 0 | −2.2 | −0.8 | 50 |
| 889 | 4 | 6.5 | 0 | −2.2 | −0.6 | 50 |
| 890 | 4 | 6.5 | 0 | −2.3 | −0.1 | 50 |
| 891 | 4 | 6.5 | 0 | −2.2 | 0 | 50 |
| 892 | 4 | 6.5 | 0 | −2.2 | 1 | 50 |
| 893 | 4 | 6.5 | 0 | −2.1 | 1.3 | 50 |
| 894 | 4 | 6.5 | 0 | −2 | 1.4 | 50 |
| 895 | 4 | 6.5 | 0 | −2 | 1.5 | 50 |
| 896 | 4 | 6.5 | 0 | −1.7 | 2 | 50 |
| 897 | 4 | 6.5 | 0 | −1.6 | 2.1 | 50 |
| 898 | 4 | 6.5 | 0 | −1.2 | 2.1 | 50 |
| 899 | 4 | 6.5 | 0 | −1.2 | 2.3 | 50 |

APPENDIX I-continued

| | | | | | | |
|---|---|---|---|---|---|---|
| 900 | 4 | 6.5 | 0 | −1.2 | 2.4 | 50 |
| 901 | 4 | 6.5 | 0 | −1 | 2.2 | 50 |
| 902 | 4 | 6.5 | 0 | −0.8 | 2.4 | 50 |
| 903 | 4 | 6.5 | 0 | −0.8 | 2.5 | 50 |
| 904 | 4 | 6.5 | 0 | −0.6 | 2.6 | 50 |
| 905 | 4 | 6.5 | 0 | −0.2 | 2.7 | 50 |
| 906 | 4 | 6.5 | 0 | −0.2 | 2.7 | 50 |
| 907 | 4 | 6.5 | 0 | −0.1 | 2.7 | 50 |
| 908 | 4 | 6.5 | 0 | 0.2 | 2.7 | 50 |
| 909 | 4 | 6.5 | 0 | 0.7 | 2.4 | 50 |
| 910 | 4 | 6.5 | 0 | 2.4 | 0.6 | 50 |
| 911 | 4 | 6.5 | 0 | 2.4 | −0.4 | 50 |
| 912 | 4 | 6.5 | 0 | 2.4 | −0.6 | 50 |
| 913 | 4 | 6.5 | 0 | 2.2 | −1.3 | 50 |
| 914 | 4 | 6.5 | 0 | 1.8 | −1.7 | 50 |
| 915 | 4 | 6.5 | 0 | 1.5 | −2.1 | 50 |
| 916 | 4 | 6.5 | 0 | 1.1 | −2.2 | 50 |
| 917 | 4 | 6.5 | 0 | 0.9 | −2.3 | 50 |
| 918 | 4 | 6.5 | 0 | 0.9 | −2.5 | 50 |
| 919 | 4 | 6.5 | 0 | 0.4 | −2.6 | 50 |
| 920 | 4 | 6.5 | 0 | 0.2 | −2.6 | 50 |
| 921 | 4 | 6.5 | 0 | −0.2 | −2.7 | 50 |
| 922 | 4 | 6.5 | 0 | −1 | −2.3 | 50 |
| 923 | 4 | 6.5 | 0 | −1.1 | −2.3 | 50 |
| 924 | 4 | 6.5 | 0 | −1.2 | 2.5 | 50 |
| 925 | 4 | 6.5 | 0 | −0.9 | 2.7 | 50 |
| 926 | 4 | 6.5 | 0 | −0.6 | 2.7 | 50 |
| 927 | 4 | 6.5 | 0 | 0.3 | 2.7 | 50 |
| 928 | 4 | 6.5 | 0 | 0.6 | 2.7 | 50 |
| 929 | 4 | 6.5 | 0 | 0.7 | 2.7 | 50 |
| 930 | 4 | 6.5 | 0 | 1.2 | −2.6 | 50 |
| 931 | 4 | 6.5 | 0 | 1.1 | −2.5 | 50 |
| 932 | 4 | 6.5 | 0 | 0.9 | −2.6 | 50 |
| 933 | 4 | 6.5 | 0 | 0.7 | −2.7 | 50 |
| 934 | 4 | 6.5 | 0 | 0.4 | −2.7 | 50 |
| 935 | 4 | 6.5 | 0 | 0.4 | −2.7 | 50 |
| 936 | 4 | 6.5 | 0 | −0.8 | −2.6 | 50 |
| 937 | 4.5 | 6.5 | 0 | −0.5 | 1.4 | 63 |
| 938 | 4.5 | 6.5 | 0 | 1.1 | −0.8 | 63 |
| 939 | 4.5 | 6.5 | 0 | −1.8 | 0.4 | 63 |
| 940 | 4.5 | 6.5 | 0 | −1.8 | 0.7 | 63 |
| 941 | 4.5 | 6.5 | 0 | −1.5 | 0.9 | 63 |
| 942 | 4.5 | 6.5 | 0 | −1.6 | 1.1 | 63 |
| 943 | 4.5 | 6.5 | 0 | −1.6 | 1.2 | 63 |
| 944 | 4.5 | 6.5 | 0 | −0.9 | 1.6 | 63 |
| 945 | 4.5 | 6.5 | 0 | −0.7 | 1.8 | 63 |
| 946 | 4.5 | 6.5 | 0 | 1.9 | 0.4 | 63 |
| 947 | 4.5 | 6.5 | 0 | 1.9 | 0 | 63 |
| 948 | 4.5 | 6.5 | 0 | 1.4 | −0.9 | 63 |
| 949 | 4.5 | 6.5 | 0 | 1.5 | −1.3 | 63 |
| 950 | 4.5 | 6.5 | 0 | 0.6 | −1.8 | 63 |
| 951 | 4.5 | 6.5 | 0 | −1.9 | 0.8 | 63 |
| 952 | 4.5 | 6.5 | 0 | −1.8 | 1.2 | 63 |
| 953 | 4.5 | 6.5 | 0 | −1.7 | 1.5 | 63 |
| 954 | 4.5 | 6.5 | 0 | −1.6 | 1.8 | 63 |
| 955 | 4.5 | 6.5 | 0 | −1.4 | 1.7 | 63 |
| 956 | 4.5 | 6.5 | 0 | −1.3 | 1.9 | 63 |
| 957 | 4.5 | 6.5 | 0 | −0.9 | 1.8 | 63 |
| 958 | 4.5 | 6.5 | 0 | −0.2 | 2.3 | 63 |
| 959 | 4.5 | 6.5 | 0 | 2.1 | −0.1 | 63 |
| 960 | 4.5 | 6.5 | 0 | 1.8 | −1.4 | 63 |
| 961 | 4.5 | 6.5 | 0 | 1.5 | −1.5 | 63 |
| 962 | 4.5 | 6.5 | 0 | 1.4 | −1.8 | 63 |
| 963 | 4.5 | 6.5 | 0 | 1.4 | −1.8 | 63 |
| 964 | 4.5 | 6.5 | 0 | 1.4 | −1.9 | 63 |
| 965 | 4.5 | 6.5 | 0 | 0.9 | −2.2 | 63 |
| 966 | 4.5 | 6.5 | 0 | 0.7 | −2 | 63 |
| 967 | 4.5 | 6.5 | 0 | 0.7 | −2.3 | 63 |
| 968 | 4.5 | 6.5 | 0 | 0.2 | −2.3 | 63 |
| 969 | 4.5 | 6.5 | 0 | −0.3 | −2.3 | 63 |
| 970 | 4.5 | 6.5 | 0 | −1.7 | 1.8 | 63 |
| 971 | 4.5 | 6.5 | 0 | −0.9 | 2.3 | 63 |
| 972 | 4.5 | 6.5 | 0 | −0.7 | 2.4 | 63 |
| 973 | 5 | 6.5 | 0 | −1.2 | 0.4 | 77 |
| 974 | 5 | 6.5 | 0 | −1.1 | 1 | 77 |
| 975 | 5 | 6.5 | 0 | −1 | 1.2 | 77 |
| 976 | 5 | 6.5 | 0 | 1.1 | −0.6 | 77 |
| 977 | 5 | 6.5 | 0 | 0.9 | −1.2 | 77 |
| 978 | 5 | 6.5 | 0 | −1.7 | 0.7 | 77 |
| 979 | 5 | 6.5 | 0 | −1.7 | 0.9 | 77 |
| 980 | 5 | 6.5 | 0 | −1.4 | 1 | 77 |
| 981 | 5 | 6.5 | 0 | −1.4 | 1.2 | 77 |
| 982 | 5 | 6.5 | 0 | −1.3 | 1.3 | 77 |
| 983 | 5 | 6.5 | 0 | −1.1 | 1.5 | 77 |
| 984 | 5 | 6.5 | 0 | −0.5 | 1.8 | 77 |
| 985 | 5 | 6.5 | 0 | 1.7 | −0.5 | 77 |
| 986 | 5 | 6.5 | 0 | 1.4 | −1.1 | 77 |
| 987 | 5 | 6.5 | 0 | 1.1 | −1.6 | 77 |
| 988 | 5 | 6.5 | 0 | 0.8 | −1.5 | 77 |
| 989 | 5 | 6.5 | 0 | 0.8 | −1.8 | 77 |
| 990 | 5 | 6.5 | 0 | 0.1 | −1.7 | 77 |
| 991 | 5 | 6.5 | 0 | 0 | −2 | 77 |
| 992 | 5 | 6.5 | 0 | −1.9 | −0.1 | 77 |
| 993 | 5 | 6.5 | 0 | −2 | 0.3 | 77 |
| 994 | 5 | 6.5 | 0 | −1.7 | 1.1 | 77 |
| 995 | 5 | 6.5 | 0 | −1.2 | 1.7 | 77 |
| 996 | 5 | 6.5 | 0 | −0.8 | 2 | 77 |
| 997 | 5 | 6.5 | 0 | −0.7 | 2.2 | 77 |
| 998 | 5 | 6.5 | 0 | −0.5 | 2.2 | 77 |
| 999 | 5 | 6.5 | 0 | −0.4 | 2.2 | 77 |
| 1000 | 5 | 6.5 | 0 | 0.5 | 2.2 | 77 |
| 1001 | 5 | 6.5 | 0 | 1.8 | −1 | 77 |
| 1002 | 5 | 6.5 | 0 | 1.4 | −1.5 | 77 |
| 1003 | 5 | 6.5 | 0 | 1.3 | −1.7 | 77 |
| 1004 | 5 | 6.5 | 0 | 1.1 | −1.9 | 77 |
| 1005 | 5 | 6.5 | 0 | 0.7 | −1.9 | 77 |
| 1006 | 5 | 6.5 | 0 | 0.8 | −2.2 | 77 |
| 1007 | 5 | 6.5 | 0 | −0.6 | −2.2 | 77 |
| 1008 | 5.5 | 6.5 | 0 | −0.8 | 0.7 | 91 |
| 1009 | 5.5 | 6.5 | 0 | −0.3 | 0.8 | 91 |
| 1010 | 5.5 | 6.5 | 0 | 0.8 | −0.9 | 91 |
| 1011 | 5.5 | 6.5 | 0 | −1.2 | 0.3 | 91 |
| 1012 | 5.5 | 6.5 | 0 | −1.4 | 0.7 | 91 |
| 1013 | 5.5 | 6.5 | 0 | −0.6 | 1.2 | 91 |
| 1014 | 5.5 | 6.5 | 0 | −0.5 | 1.2 | 91 |
| 1015 | 5.5 | 6.5 | 0 | 1.4 | 0 | 91 |
| 1016 | 5.5 | 6.5 | 0 | 1.4 | −0.6 | 91 |
| 1017 | 5.5 | 6.5 | 0 | 1.2 | −0.7 | 91 |
| 1018 | 5.5 | 6.5 | 0 | 0.9 | −1.2 | 91 |
| 1019 | 5.5 | 6.5 | 0 | 0.8 | −1.1 | 91 |
| 1020 | 5.5 | 6.5 | 0 | −1.5 | 0.6 | 91 |
| 1021 | 5.5 | 6.5 | 0 | −0.8 | 1.4 | 91 |
| 1022 | 5.5 | 6.5 | 0 | −0.9 | 1.7 | 91 |
| 1023 | 5.5 | 6.5 | 0 | −0.8 | 1.8 | 91 |
| 1024 | 5.5 | 6.5 | 0 | −0.7 | 1.7 | 91 |
| 1025 | 5.5 | 6.5 | 0 | −0.5 | 1.8 | 91 |
| 1026 | 5.5 | 6.5 | 0 | 1.7 | 0.1 | 91 |
| 1027 | 5.5 | 6.5 | 0 | 1.7 | −0.4 | 91 |
| 1028 | 5.5 | 6.5 | 0 | 1.3 | −1 | 91 |
| 1029 | 5.5 | 6.5 | 0 | 1.3 | −1.2 | 91 |
| 1030 | 5.5 | 6.5 | 0 | 1.2 | −1.6 | 91 |
| 1031 | 5.5 | 6.5 | 0 | 1 | −1.4 | 91 |
| 1032 | 5.5 | 6.5 | 0 | 0.7 | −1.7 | 91 |
| 1033 | 5.5 | 6.5 | 0 | 0.6 | −1.6 | 91 |
| 1034 | 5.5 | 6.5 | 0 | 0.6 | −1.8 | 91 |
| 1035 | 5.5 | 6.5 | 0 | −0.4 | −1.8 | 91 |
| 1036 | 6 | 6.5 | 0 | −0.6 | 0.4 | 111 |
| 1037 | 6 | 6.5 | 0 | −0.4 | 0.7 | 111 |
| 1038 | 6 | 6.5 | 0 | 0.7 | −0.3 | 111 |
| 1039 | 6 | 6.5 | 0 | 0.7 | −0.4 | 111 |
| 1040 | 6 | 6.5 | 0 | 0.7 | −0.4 | 111 |
| 1041 | 6 | 6.5 | 0 | −1.1 | 0.3 | 111 |
| 1042 | 6 | 6.5 | 0 | −0.8 | 0.5 | 111 |
| 1043 | 6 | 6.5 | 0 | −0.5 | 1.1 | 111 |
| 1044 | 6 | 6.5 | 0 | 1.1 | 0.1 | 111 |
| 1045 | 6 | 6.5 | 0 | 1.1 | −0.5 | 111 |
| 1046 | 6 | 6.5 | 0 | 0.6 | −0.6 | 111 |
| 1047 | 6 | 6.5 | 0 | 0.7 | −0.8 | 111 |
| 1048 | 6 | 6.5 | 0 | 0.7 | −0.9 | 111 |
| 1049 | 6 | 6.5 | 0 | 0.5 | −0.7 | 111 |
| 1050 | 6 | 6.5 | 0 | 0.4 | −0.8 | 111 |
| 1051 | 6 | 6.5 | 0 | −0.9 | 1.1 | 111 |
| 1052 | 6 | 6.5 | 0 | −0.5 | 1.2 | 111 |
| 1053 | 6 | 6.5 | 0 | 1.2 | −0.5 | 111 |
| 1054 | 6 | 6.5 | 0 | 1 | −1.2 | 111 |
| 1055 | 6 | 6.5 | 0 | 0.7 | −1.1 | 111 |
| 1056 | 6 | 6.5 | 0 | 0.7 | −1.4 | 111 |
| 1057 | 6 | 6.5 | 0 | 0.4 | −1.3 | 111 |

APPENDIX I-continued

| | | | | | | |
|---|---|---|---|---|---|---|
| 1058 | 6 | 6.5 | 0 | −1.3 | 0 | 111 |
| 1059 | 6 | 6.5 | 0 | −1.2 | 1.1 | 111 |
| 1060 | 6 | 6.5 | 0 | 0.6 | −1.7 | 111 |
| 1061 | 6 | 6.5 | 0 | 0.5 | −1.7 | 111 |
| 1062 | 6.5 | 6.5 | 0 | −0.6 | 0.2 | 125 |
| 1063 | 6.5 | 6.5 | 0 | −0.5 | 0.4 | 125 |
| 1064 | 6.5 | 6.5 | 0 | −0.4 | 0.7 | 125 |
| 1065 | 6.5 | 6.5 | 0 | −0.7 | 0 | 125 |
| 1066 | 6.5 | 6.5 | 0 | −0.6 | 1 | 125 |
| 1067 | 6.5 | 6.5 | 0 | −0.4 | 0.8 | 125 |
| 1068 | 6.5 | 6.5 | 0 | 0.6 | 0.9 | 125 |
| 1069 | 6.5 | 6.5 | 0 | 0.7 | −0.5 | 125 |
| 1070 | 6.5 | 6.5 | 0 | 0.6 | −0.6 | 125 |
| 1071 | 6.5 | 6.5 | 0 | 0.3 | −0.8 | 125 |
| 1072 | 6.5 | 6.5 | 0 | −1 | −0.3 | 125 |
| 1073 | 6.5 | 6.5 | 0 | −0.9 | 0.9 | 125 |
| 1074 | 6.5 | 6.5 | 0 | −0.5 | 1.3 | 125 |
| 1075 | 6.5 | 6.5 | 0 | −0.3 | 1.4 | 125 |
| 1076 | 6.5 | 6.5 | 0 | −0.2 | 1.2 | 125 |
| 1077 | 6.5 | 6.5 | 0 | 0.9 | −1.1 | 125 |
| 1078 | 6.5 | 6.5 | 0 | 0.5 | −1.2 | 125 |
| 1079 | 6.5 | 6.5 | 0 | −0.9 | −0.9 | 125 |

What is claimed is:

1. A method of treating an eye with a laser, the method comprising:
    making a beam of an ablative light energy with the laser;
    varying a dimension across the laser beam during a treatment of the eye; and
    varying a firing rate of the laser during the treatment in correlation with the varying of the dimension across the beam.

2. The method of claim 1 wherein the varying of the dimension across the beam and the varying of the firing rate are arranged so as to maintain a power of the beam applied to the eye at a substantially constant level during at least a portion of the treatment.

3. The method of claim 1 wherein the dimension across the beam varies between a first size and a second size, an amount of energy applied to the eye with a first pulse of the laser beam being lower at the first size than an amount of energy applied to the eye with a second pulse of the laser beam at the second size, and wherein the firing rate varies between a first firing rate at the first size and a second rate at the second size, the first firing rate being faster than the second firing rate.

4. The method of claim 3 wherein the dimension across the beam varies by at least 3 mm during the ablative treatment.

5. The method of claim 1 wherein the dimension across the beam varies between a first size and a second size, an amount of energy applied to the eye with a first pulse of the laser beam being higher at the first size than an amount of energy applied to the eye with a second pulse of the laser beam at the second size, and wherein the firing rate varies between a first firing rate at the first size and a second firing rate at the second size, the first rate being slower than the second firing rate.

6. The method of claim 1 further comprising scanning the laser beam over a treatment area of the eye.

7. The method of claim 1 wherein the dimension across the beam varies by at least 0.5 mm during the ablative treatment.

8. The method of claim 1 wherein the firing rate of the laser varies by at least 2 Hz during the treatment.

9. The method of claim 8 wherein the firing rate of the laser varies by at least 10 Hz during the treatment.

10. The method of claim 1 wherein the laser is a pulsed laser, and the laser beam is a pulsed laser beam having a pulse duration.

11. The method of claim 10 further comprising a step of delaying the firing of the pulsed laser in response to predetermined value.

12. A method for treating an eye, the method comprising:
    directing a series of corneal ablation laser pulses toward the eye, a first pulse having a first size and a second pulse having a second size which is smaller than the first size; and
    varying a firing rate of the series in response to the sizes to effect a faster firing rate for the second pulse than during the first pulse.

13. A method for treating an eye, the method comprising:
    directing a series of corneal ablation laser pulses toward the eye a first pulse having a first size and a second pulse having a second size which is larger than the first size; and
    varying a firing rate of the series in response to the sizes to effect a slower firing rate for the second pulse than for the first pulse.

14. A system for treating an eye with a laser beam, the system comprising:
    a laser fir making a beam of an ablative light energy;
    at least one processor having a computer readable medium, the computer readable medium having a program adapted to vary a dimension across the laser beam during a treatment of the eye and vary a firing rate of the laser beam during the treatment in correlation with the dimension across the beam.

15. The system of claim 14 wherein the computer program of the computer readable medium is configured to vary the dimension across the beam and the firing rate of the laser so as to maintain a power of the beam applied to the eye at a substantially constant level during at least a portion of the treatment.

16. The system of claim 14 wherein the computer program of the computer readable medium is configured to vary the dimension across the beam between a first size and a second size, and to apply an amount of energy to the eye with a first pulse of the laser beam that is lower at the first size than an amount of energy applied to the eye with a second pulse of the laser beam at the second size, and wherein the computer program of the computer readable medium is configured to vary the firing rate between a first firing rate when the laser beam is at the first size and a second firing rate when the laser beam is at the second size, the first firing rate being faster tan the second firing rate.

17. The system of claim 14 wherein the computer program of the computer readable medium is configured to vary the dimension across the beam between a first size and a second size such tat an amount of energy applied to the eye with a first pulse of the laser beam is higher at the first size than an amount of energy applied to the eye with a second pulse of the laser beam at the second size, and wherein the computer program is configured to vary the firing rate between a first firing rate when the laser beam is at the first size and a second firing rate when the laser beam is at the second size, the first firing rate being alower then the second firing rate.

18. The system of claim 14 wherein the computer program of the computer readable medium is further adapted to scan the laser beam over a treatment area.

19. The system of claim 14 wherein the dimension across the beam varies by at least 0.5 mm during the ablative treatment.

20. The system of claim 19 wherein the dimension across the beam varies by at least 3 mm during the ablative treatment.

21. The system of claim 14 wherein the firing rate of the laser varies by at least 2 Hz during the treatment.

22. The system of claim 21 wherein the firing rate of the laser varies by at least 10 Hz during the treatment.

23. The system of claim 14 wherein the laser is a pulsed laser, and the laser beam is a pulsed laser beam having a pulse duration.

24. The system of claim 23 wherein the processor further comprises a treatment table listing a predetermined delay between sequential pulses of the pulsed laser beam.

25. A laser eye surgery system for treating an eye, the system comprising:

a laser generating a series of laser pulses for treatment of the eye;

delivery optics varying a size of the pulses from a first pulse size to a second pulse size smaller than the first size; and a controller having computer readable medium that varies a firing rate of the laser at least in part in response to the pulse size so that the firing rate is faster during the second pulse size.

26. A laser eye surgery system for treating an eye, the system comprising:

a laser generating a series of laser pulses for treatment of the eye;

delivery optics varying a size of the pulses from a first pulse size to a second pulse size larger than the first size; and a controller having a computer readable medium that varies a firing rate of the laser at least in part in response to the pulse size so that the firing rate is slower during the second pulse size.

* * * * *